United States Patent
Engel

(10) Patent No.: US 7,308,820 B2
(45) Date of Patent: *Dec. 18, 2007

(54) PIEZOCABLE BASED SENSOR FOR MEASURING UNSTEADY PRESSURES INSIDE A PIPE

(75) Inventor: Thomas W. Engel, East Hampton, CT (US)

(73) Assignee: CiDRA Corporation, Wallingford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/915,312

(22) Filed: Aug. 9, 2004

(65) Prior Publication Data

US 2005/0072216 A1 Apr. 7, 2005

Related U.S. Application Data

(60) Provisional application No. 60/529,960, filed on Dec. 15, 2003, provisional application No. 60/493,830, filed on Aug. 8, 2003.

(51) Int. Cl.
*G01N 11/00* (2006.01)

(52) U.S. Cl. .................................... 73/53.01

(58) Field of Classification Search ............... 73/53.01, 73/861.18, 170.13, 170.14, 29.03
See application file for complete search history.

(56) References Cited

U.S. PATENT DOCUMENTS

| | | | |
|---|---|---|---|
| 4,048,853 A | 9/1977 | Smith et al. | 73/861.25 |
| 4,090,404 A | 5/1978 | Ligier et al. | |
| 4,216,403 A | 8/1980 | Claassen et al. | |
| 4,248,085 A | 2/1981 | Coulthard | 73/861.06 |
| 4,376,302 A | 3/1983 | Miller et al. | |
| 4,445,389 A | 5/1984 | Potzick et al. | 73/861.27 |
| 4,638,207 A | 1/1987 | Radice et al. | |
| 4,794,295 A | 12/1988 | Penneck et al. | |

(Continued)

FOREIGN PATENT DOCUMENTS

FR 2725787 4/1996

(Continued)

OTHER PUBLICATIONS

"Piezo Film Sensors Technical Manua," Measurement Specialties, Inc. P/N 1005663-1, Rev. Apr. 2, 1999.*

(Continued)

*Primary Examiner*—Hezron Williams
*Assistant Examiner*—Rodney Frank
(74) *Attorney, Agent, or Firm*—Michael Grillo

(57) ABSTRACT

A piezocable based sensor for measuring unsteady pressures inside a pipe comprises a cable wrapped around the pipe and an outer band compressing the cable towards the pipe. The cable provides a signal indicative of unsteady pressure within the pipe in response to expansion and contraction of the pipe. The cable includes: a first electrical conductor, a piezoelectric material disposed around the first electrical conductor, a second electrical conductor disposed around the piezoelectric material, and an insulative jacket surrounding the piezoelectric material and electrical conductors. The cable may be part of an array of cables wrapped around the pipe, and a signal processor may determine a parameter of the fluid using the signals. A housing is disposed around the pipe and electrical components associated with the pipe. Ends of the housing include a sealing arrangement, which provides a seal between the ends of the housing and the pipe.

56 Claims, 24 Drawing Sheets

U.S. PATENT DOCUMENTS

| | | | |
|---|---|---|---|
| 4,896,540 A | 1/1990 | Shakkottai et al. | 73/861.02 |
| 5,131,278 A | 7/1992 | Baumoel | |
| 5,218,197 A | 6/1993 | Carroll | 250/227.19 |
| 5,285,675 A | 2/1994 | Colgate et al. | 73/23.2 |
| 5,357,486 A | 10/1994 | Pearce | 367/159 |
| 5,367,911 A | 11/1994 | Jewell et al. | 73/861.08 |
| 5,398,542 A | 3/1995 | Vasbinder | 73/40.5 |
| 5,550,791 A | 8/1996 | Peloquin | |
| 5,591,922 A | 1/1997 | Segeral et al. | 73/861.04 |
| 5,741,980 A | 4/1998 | Hill et al. | 73/861.04 |
| 5,770,805 A | 6/1998 | Castel | 73/861.04 |
| 5,770,806 A | 6/1998 | Hiismaki | 73/861.29 |
| 5,835,884 A | 11/1998 | Brown | 73/861.04 |
| 5,845,033 A | 12/1998 | Berthold et al. | 385/12 |
| 5,948,959 A | 9/1999 | Peloquin | 73/1.83 |
| 6,016,702 A | 1/2000 | Maron | 73/705 |
| 6,202,494 B1 | 3/2001 | Ricbel et al. | 73/861.29 |
| 6,271,621 B1* | 8/2001 | Ito et al. | 310/358 |
| 6,354,147 B1* | 3/2002 | Gysling et al. | 73/61.79 |
| 6,435,030 B1 | 8/2002 | Gysling et al. | 73/587 |
| 6,450,037 B1 | 9/2002 | McGuinn et al. | 73/705 |
| 6,536,291 B1 | 3/2003 | Gysling et al. | 73/861.42 |
| 6,587,798 B2 | 7/2003 | Kersey et al. | 702/50 |
| 6,609,069 B2 | 8/2003 | Gysling | 702/48 |
| 6,691,584 B2 | 2/2004 | Gysling et al. | 73/861.42 |
| 6,736,904 B2* | 5/2004 | Poniatowski et al. | 134/1 |
| 6,782,150 B2 | 8/2004 | Davis et al. | 385/12 |
| 6,889,562 B2 | 5/2005 | Gysling et al. | 73/861.42 |
| 6,898,541 B2 | 5/2005 | Gysling et al. | 702/100 |
| 6,945,095 B2 | 9/2005 | Johansen | |
| 6,959,604 B2 | 11/2005 | Davis et al. | |
| 6,971,259 B2 | 12/2005 | Gysling | |
| 7,058,549 B2 | 6/2006 | Croteau et al. | |
| 7,086,278 B2 | 8/2006 | Gysling et al. | |
| 7,146,864 B2* | 12/2006 | Sullivan et al. | 73/861.42 |
| 2002/0064331 A1* | 5/2002 | Davis et al. | 385/12 |
| 2002/0097637 A1* | 7/2002 | Pearce et al. | 367/154 |
| 2003/0010126 A1* | 1/2003 | Romanet et al. | 73/649 |
| 2003/0154036 A1 | 8/2003 | Gysling et al. | |
| 2004/0016284 A1 | 1/2004 | Gysling et al. | |
| 2004/0069069 A1* | 4/2004 | Gysling et al. | 73/736 |
| 2004/0074312 A1 | 4/2004 | Gysling | |
| 2004/0168522 A1* | 9/2004 | Fernald et al. | 73/861.01 |
| 2004/0168523 A1* | 9/2004 | Fernald et al. | 73/861.01 |
| 2004/0210404 A1 | 10/2004 | Gysling et al. | |
| 2004/0231431 A1* | 11/2004 | Sullivan et al. | 73/861.42 |
| 2005/0005711 A1 | 1/2005 | Curry et al. | |
| 2005/0005912 A1 | 1/2005 | Gysling et al. | |
| 2005/0011283 A1 | 1/2005 | Gysling et al. | |
| 2005/0011284 A1 | 1/2005 | Davis et al. | |
| 2005/0039520 A1* | 2/2005 | Davis et al. | 73/49.5 |
| 2005/0044966 A1* | 3/2005 | Gysling et al. | 73/861.26 |
| 2005/0227538 A1 | 10/2005 | Engel | |
| 2007/0027638 A1* | 2/2007 | Fernald et al. | 702/25 |
| 2007/0044571 A1* | 3/2007 | Gysling et al. | 73/861.18 |

FOREIGN PATENT DOCUMENTS

| | | |
|---|---|---|
| GB | 2282931 | 4/1995 |
| WO | WO 93/14382 | 7/1993 |
| WO | WO 99/67629 | 12/1999 |
| WO | WO 00/60317 | 10/2000 |
| WO | WO 01/02810 | 1/2001 |
| WO | WO 03 062759 | 7/2003 |

OTHER PUBLICATIONS

"Development of an array of pressure sensors with PVDF film," Experiments in Fluids 26, Jan. 8, 1999.*

"Mass Fraction Measurements in Multiphase Flow using a Clamp on PVDF Array", Johan Carlson, Oct. 2000.

"PVDF and Array Transducers", Robert A. Day, NDTnet—Sep. 1996, vol. 1, No. 9.

"Polymer Piezoelectric Transducers for Ultrasonic NDE", Authors: Yhoseph Bar-Chohen, Tianji Xue And Shyh-Shiuh Lih, NDTnet—Sep. 1996, vol. 1, No. 9.

"Piezofilm Sensors Technical Manual"—Measurement Specialities, Inc. P/N 1005663-1—Rev. B Apr. 2, 2009.

"Sonar-Based Volumetric Flow Meter for Pulp and Paper Applications"—By: D. Gysling & D. Loose Dec. 3, 2002.

Sonar-Based Volumentric Flow Meter for Chemical and Petrochemical Appl'ns.—By: D. Gyslng & D. Loose—Feb. 14, 2003.

"Noise and Vibration Control Engineering Principles and Applications", Leo L. Beranek and Istvan L. Ver, A. Wiley Interscience Publication, pp. 537-541, Aug. 1992.

"Two Decades of Array Signal Processing Research", The Parametric Approach, H. Krim and M. Viberg, IEEE Signal Processing Magazine, Jul. 1996, pp. 67-94.

"Development of an array of pressure sensors with PVDF film, Experiments in Fluids 26", Jan. 8, 1999, Springer-Verlag.

"Viscous Attentuation of Acoustic Waves in Suspensions" by R.L. Gibson, Jr. and M.N. Toksoz.

* cited by examiner

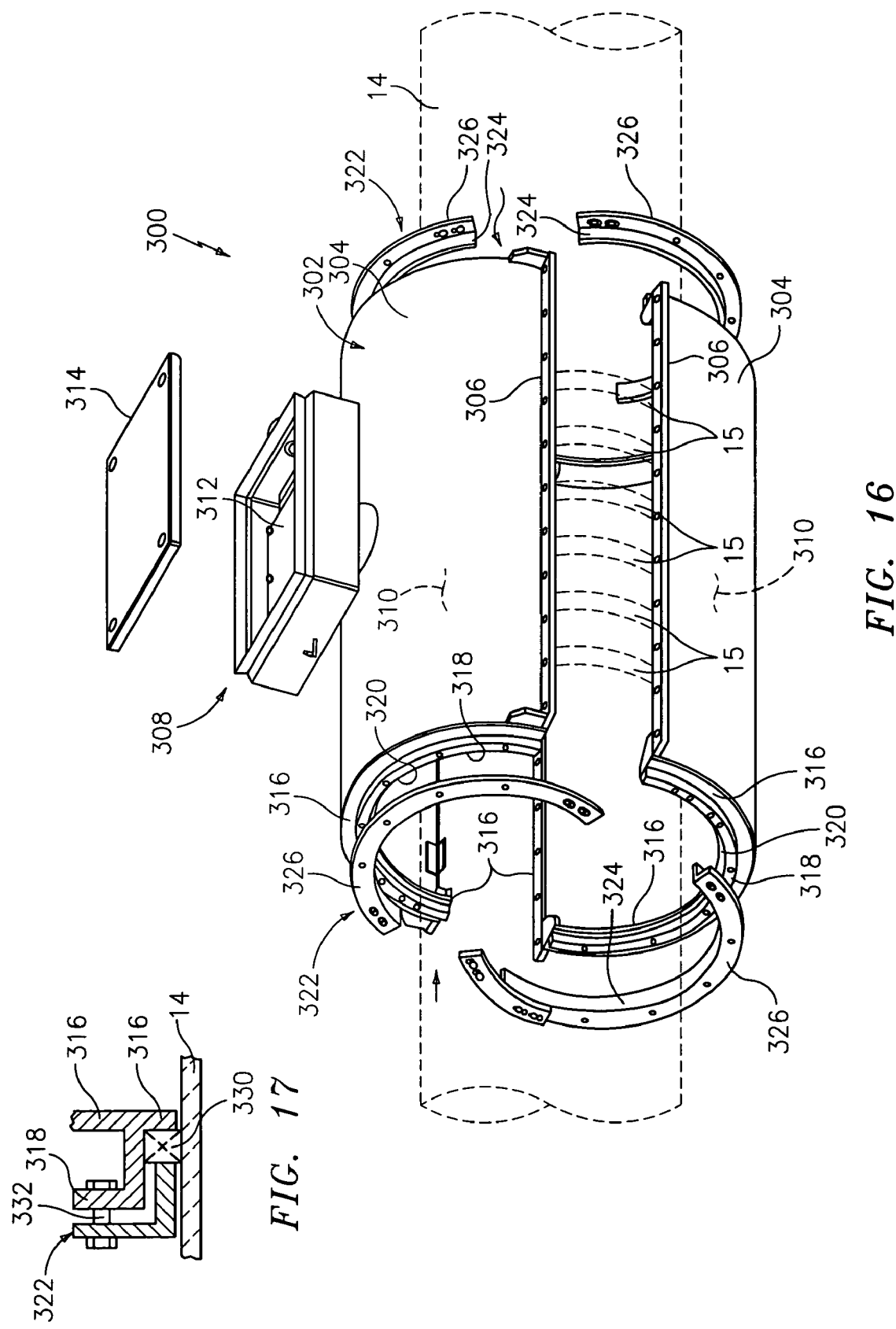

PIEZOCABLE BASED SENSOR FOR MEASURING UNSTEADY PRESSURES INSIDE A PIPE

CROSS-REFERENCE TO RELATED APPLICATIONS

This application claims the benefit of U.S. Provisional Patent Application Nos. 60/493,830 filed Aug. 8, 2003, and 60/529,960 filed Dec. 15, 2003, both of which are incorporated herein by reference.

BACKGROUND OF THE INVENTION

1. Technical Field

The present invention generally relates to an apparatus for measuring unsteady pressures inside a pipe; and more particularly to an apparatus for measuring the same using a piezocable based sensor disposed on an outer surface of the pipe.

2. Background

A fluid flow process (flow process) includes any process that involves the flow of fluid through pipe, ducts, or other conduits, as well as through fluid control devices such as pumps, valves, orifices, heat exchangers, and the like. Flow processes are found in many different industries such as the oil and gas industry, refining, food and beverage industry, chemical and petrochemical industry, pulp and paper industry, power generation, pharmaceutical industry, and water and wastewater treatment industry. The fluid within the flow process may be a single phase fluid (e.g., gas, liquid or liquid/liquid mixture) and/or a multi-phase mixture (e.g. paper and pulp slurries or other solid/liquid mixtures). The multi-phase mixture may be a two-phase liquid/gas mixture, a solid/gas mixture or a solid/liquid mixture, gas entrained liquid or a three-phase mixture.

Various sensing technologies exist for measuring various physical parameters of single and/or multiphase fluids in an industrial flow process. Such physical parameters include, for example, volumetric flow rate, composition, consistency, density, and mass flow rate. Problematically, many sensors must be placed in contact with the fluid and, as a result, cannot be installed, moved or otherwise reconfigured without shutting down a portion of the flow process to install the sensors.

Various non-intrusive sensors have been developed, which are attached to the surface of the pipe. Such sensors include, for example, the ultrasonic transmitter and receiver found in ultrasonic flow meters. While ultrasonic flow meters perform well for certain applications, they are generally limited to use with certain fluid types and/or temperatures. Moreover, precise alignment of the ultrasonic transmitter and receiver pair is required, which may not lend itself to instrument portability and adaptability to different pipe sizes.

In some cases, sensors are subjected to severe environmental conditions, such as high temperatures, water spray, precipitation, unintended contact, and the like. Where sensors are used in such conditions, they must be robustly designed to withstand these conditions while maintaining accuracy.

Thus, there remains a need for a robust, non-invasive sensor for measuring various parameters of single and/or multiphase fluids in an industrial flow process that is easily installed and which may be adaptable to different pipe sizes.

SUMMARY OF THE INVENTION

The above-described and other needs are met by a piezocable based sensor for measuring unsteady pressures inside a pipe. The sensor comprises a cable wrapped around the pipe and a band wrapped around the cable to compresses the cable toward the pipe. The cable includes: a first electrical conductor, a piezoelectric material disposed around the first electrical conductor and a second electrical conductor disposed around the piezoelectric material. The cable may also include a dielectric jacket disposed around the piezoelectric material, the first electrical conductor, and the second electrical conductor. The cable provides a signal indicative of unsteady pressure within the pipe in response to expansion and contraction of the pipe. The cable may be wrapped around the pipe at least one time. The piezoelectric material may include PVDF.

The cable may be part of an array of cables wrapped around the pipe. Each cable in the array of cables provides a pressure signal indicative of unsteady pressure within the pipe at a corresponding axial location along the pipe, and a signal processor determines a parameter of the fluid using the signals from the array of cables. The parameter of the fluid may includes at least one of: density of the fluid, volumetric flow rate of the fluid, mass flow rate of the fluid, composition of the fluid, entrained air in the fluid, consistency of the fluid, size of particles in the fluid, and health of a device causing the unsteady pressures to be generated in the pipe.

In various embodiments, an alignment sheet is disposed between the cable and the pipe. The alignment sheet includes tabs protruding therefrom defining a raceway for receiving the cable. The alignment sheet may include a cable inlet bumper and a cable exit bumper attached thereto. The cable inlet bumper is positioned on one side of the sensor raceway and has a radiused surface formed thereon around which a first end of the cable is bent. The cable exit bumper is positioned on an opposite side of the sensor raceway and has a radiused surface formed thereon around which a second end of the cable is bent. The alignment sheet may further include cable inlet belay and a cable exit belay attached thereto. The cable inlet belay releasably retains the first end of the cable, and the cable exit belay releasably retains the second end of the cable. The cable inlet belay and the cable exit belay may each be disposed on removable straps disposed around the alignment sheet. An electrical insulator may be disposed between the alignment sheet and the pipe, and a lubricant material may be disposed between the cable and the band.

In another aspect of the invention, a housing is provided for electrical components associated with a pipe. The electrical components may include the piezocable based sensor and associated electronics. The housing comprises a shell disposed around the pipe and the electrical components. Each end of the shell forms an annular chamber with an outer surface of the pipe. Gland rings are disposed around the pipe, with a portion of each gland ring being received within a respective chamber. Tightening the gland rings to the shell compresses packing material within the chamber to provide a seal between the ends of the shell and the pipe. The shell and gland ring may be formed from sections, allowing them to be disposed around the pipe in situ.

In another aspect of the invention, a method of installing an apparatus for measuring at least one parameter of a fluid flowing within a pipe comprises: (a) wrapping a cable around a pipe; (b) wrapping a band around the cable; (c) tightening the band around the cable to compress the cable toward the pipe; and (d) electrically connecting the cable to a signal processor. The cable includes: a first electrical conductor, a piezoelectric material disposed around the first electrical conductor, and a second electrical conductor disposed around the piezoelectric material. The cable may also include a dielectric jacket disposed around the piezoelectric material, the first electrical conductor, and the second electrical conductor. The cable may be wrapped around the pipe at least one time. The piezoelectric material may include PVDF.

The cable provides a signal indicative of unsteady pressure within the pipe in response to expansion and contraction of the pipe, and the signal processor determines a parameter of the fluid using the signal from the cable. The parameter of the fluid may include at least one of: density of the fluid, volumetric flow rate of the fluid, mass flow rate of the fluid, composition of the fluid, entrained air in the fluid, consistency of the fluid, size of particles in the fluid, and health of a device causing the unsteady pressures to be generated in the pipe.

The method may include repeating (a) through (d) for each cable in a plurality of cables to form an array of cables wrapped around the pipe, wherein each cable in the array of cables provides a pressure signal indicative of unsteady pressure within the pipe at a corresponding axial location along the pipe, and the signal processor determines the parameter of the fluid using the signals from the array of cables.

The method may further comprise: attaching an alignment sheet to the pipe, with the alignment sheet including tabs protruding therefrom and defining a raceway for receiving the cable. The method may further comprise retaining a first end of the cable in a cable inlet belay coupled to the alignment sheet before wrapping the cable; and retaining a second end of the cable in a cable exit belay coupled to the alignment sheet after wrapping the cable. The method may also comprise: bending the cable around a radiused surface of a cable inlet bumper before wrapping the cable, the cable inlet bumper being attached to the alignment sheet; and bending the cable around a radiused surface of a cable exit bumper after wrapping the cable, the cable exit bumper being attached to the alignment sheet. The cable inlet belay and the cable exit belay may be removed after tightening the strap around the cable. An electrical insulator may be disposed between the alignment sheet and the pipe, and a lubricant material may be disposed between the cable and the band.

The foregoing and other objects, features and advantages of the present invention will become more apparent in light of the following detailed description of exemplary embodiments thereof.

BRIEF DESCRIPTION OF THE DRAWING

Referring now to the drawing wherein like items are numbered alike in the various Figures:

FIG. 16 is an exploded perspective view a housing for electrical components associated with the pipe, in accordance with an embodiment of the present invention.

FIG. 17 is a partial cross-sectional view of a sealing arrangement at an end of the housing, in accordance with an embodiment of the present invention.

DETAILED DESCRIPTION

Figure 1:
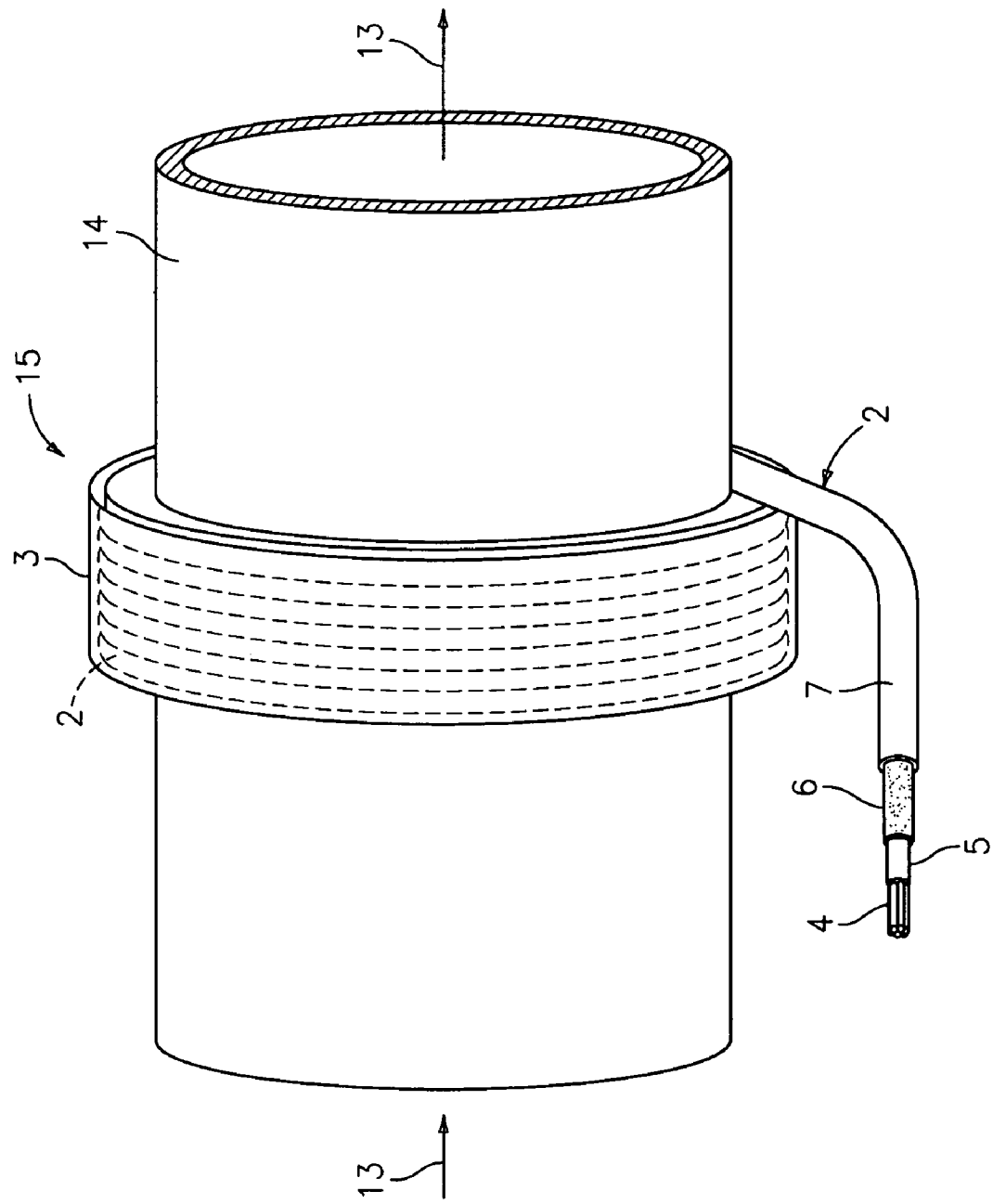
FIG. 1 is a schematic depiction of a piezocable based sensor for measuring unsteady pressures inside a pipe, in accordance with an embodiment of the present invention.

Referring to FIG. 1, a schematic depiction of a piezocable based sensor 15 for measuring unsteady pressures inside a pipe 14 is shown. The sensor 15 comprises a cable 2 wrapped around the pipe 14 and a band 3 wrapped around the cable 2 to compress the cable 2 toward the pipe 14. The cable 2 includes: an inner (first) electrical conductor 4, a piezoelectric material 5 disposed around the inner electrical conductor 4, an outer (second) electrical conductor 6 disposed around the piezoelectric material 5, and a dielectric jacket 7 disposed around the piezoelectric material 5 and the inner and outer electrical conductors 4, 6.

The cable 2 provides a signal indicative of unsteady pressure within the pipe 14 in response to expansion and contraction of the pipe 14. More specifically, expansion and contraction of the pipe 14, as may be caused by one or both of acoustic waves propagating through a fluid 13 within the pipe and/or pressure disturbances that connect with the fluid 13 flowing in the pipe 14 (e.g., turbulent eddies and vertical disturbances), cause the cable 2 to be strained longitudinally and/or strained radially against the outer band 3. In response to this longitudinal and/or radial strain, the piezoelectric material 5 generates a varying electrical charge between the inner and outer conductors 4, 6. The electrical charge varies in proportion to the amount of longitudinal and/or radial strain, and thus provides indication of the amount of expansion and contraction of the pipe 14 and, therefore, provides indication of the acoustic waves propagating through the fluid 13 within the pipe 14 and/or pressure disturbances that connect with the fluid 13 flowing in the pipe 14. The varying electrical charge, which may be amplified, impedance converted, and otherwise conditioned (e.g., filtered), is provided as the output signal from the sensor 1. As will be discussed in further detail hereinafter, this signal may be used to determine one or more parameters of the fluid 13, such as: density of the fluid 13, volumetric flow rate of the fluid 13, mass flow rate of the fluid 13, composition of the fluid 13, entrained air in the fluid 13, consistency of the fluid 13, size of particles in the fluid 13, and health of a device causing the unsteady pressures to be generated in the pipe 14.

In the embodiment of FIG. 1, the cable 2 is wrapped helically around the pipe 14 six times to form six coils or turns. It is contemplated that the number of turns may be equal to one, two, three, four, five, six, seven, eight, sixteen, twenty four, or N number of turns. Generally, the sensitivity of the sensor 15 to unsteady pressures within the pipe 14 increases as the number of turns increases when used with a charge amplifier. Further, the signal to noise ratio improves as the number of turns increases, especially when use with a voltage amplifier. Also as the number of turns increases, the width of the sensor 15 relative to the longitudinal axis of the pipe 14 increases, thereby decreasing the axial resolution of the sensor 15 (i.e., it senses a wider area along the length of the pipe 14). Therefore, the number of turns used is dependent at least on the degree of sensitivity desired and the axial resolution desired.

While the present invention contemplates the cable 2 being wrapped circumferentially around the pipe to a sensor 15 that generates a signal indicative of the circumferential average of unsteady pressure within the pipe 14, the present invention contemplates that the cable may be wrapped around a portion of the circumference of the pipe.

In the embodiment of FIG. 1, the inner conductor 4 forms a core of the cable 2 and is comprised of strands of electrically conductive material (e.g., copper, aluminum, and the like). It is also contemplated that the inner conductor 4 may be solid, or may be strands or an extrusion disposed around another rigid material that forms the core of the cable 2. The piezoelectric material 5 is helically wrapped around the inner conductor 4, although the scope of the invention is intended to include embodiments in which the piezoelectric material 5 is otherwise braided, extruded, or molded around the inner conductor 4. The piezoelectric material 5 may include any piezo-active material (e.g., polyvinylidene fluoride (PVDF)), and may include copolymers of PVDF and other materials such as trifluoroethylene (TrFE) or tetrafluorethylene (TFE). For example, a description of piezoelectric materials is provided in J. S. Harrison and Z. Ounaies, Piezoelectric Polymers, NASA/CR-2001-211422 ICASE Report No. 2001-43, ICASE Mail Stop 132C NASA Langley Research Center Hampton, Va. 23681-2199, December 2001, pp. 31.

The outer conductor 6 is shown as braided strands of electrically conductive material (e.g., copper, aluminum, and the like). It is also contemplated that the outer conductor 6 may be wrapped, extruded, or deposited around the piezoelectric material 5. The jacket 7 may be formed from any electrically insulative (dielectric) material to environmentally seal the cable 2 and protect it against thermal stimulus. For example, the jacket 7 may be formed from polyethylene or the like. One example of a cable 2 that may be used with the present invention is commercially available from Measurement Specialties, Inc. of Fairfield, N.J. as part number 1005801-1 or 1005646-1. While the cable 2 has been shown and described as having a jacket 7, the present invention contemplates that a cable 2 not having an electrically insulative jacket 7. The outer conductor 6 may be grounded to ground or the amplifier ground to provide an electrical shield from electromagnetic interference.

Figure 3:
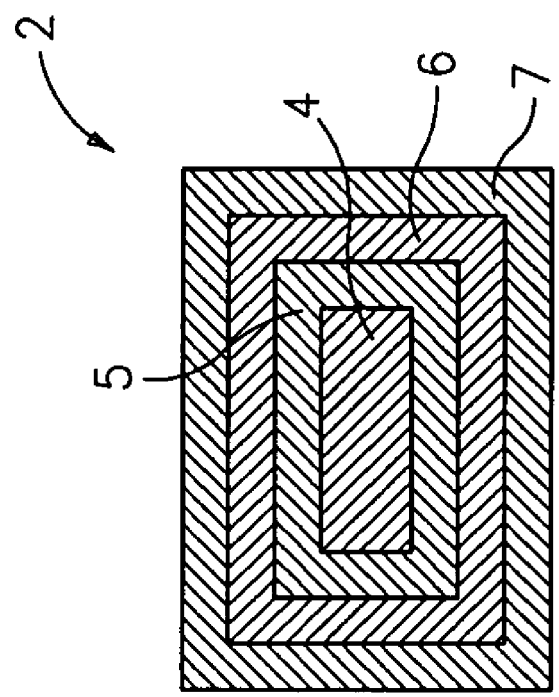
FIG. 3 is a cross-sectional view of an alternative piezocable for use with the sensor of the present invention.
Figure 2:
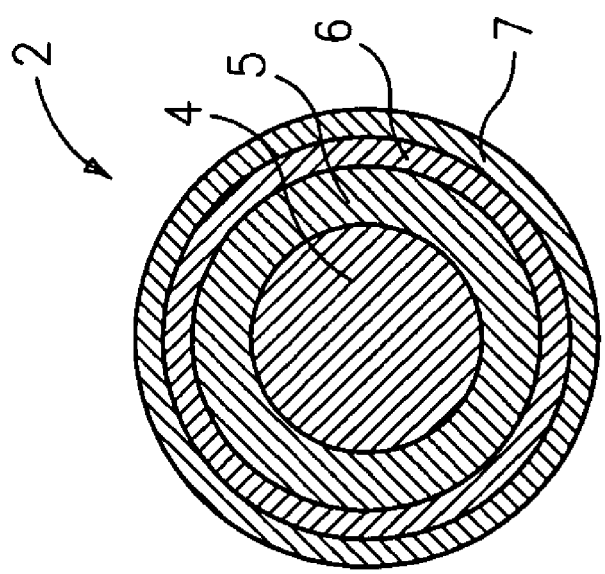
FIG. 2 is a cross-sectional view of a piezocable for use with the sensor of the present invention.

Referring to FIG. 2, the cable 2 may have a circular cross section. Alternatively, the cable 2 may have a quadrilateral (e.g., square, rectangular, etc.) cross section, as shown in FIG. 3. It is contemplated that a cable 2 of any convenient cross sectional shape may be used, such as any polygonal cross-section (e.g., triangular, hexagonal, octagonal, etc.) or generally rounded cross-section (e.g. rounded square-shaped, rounded rectangular-shaped, oblong shape, egg-shaped, oval).

Figure 4:
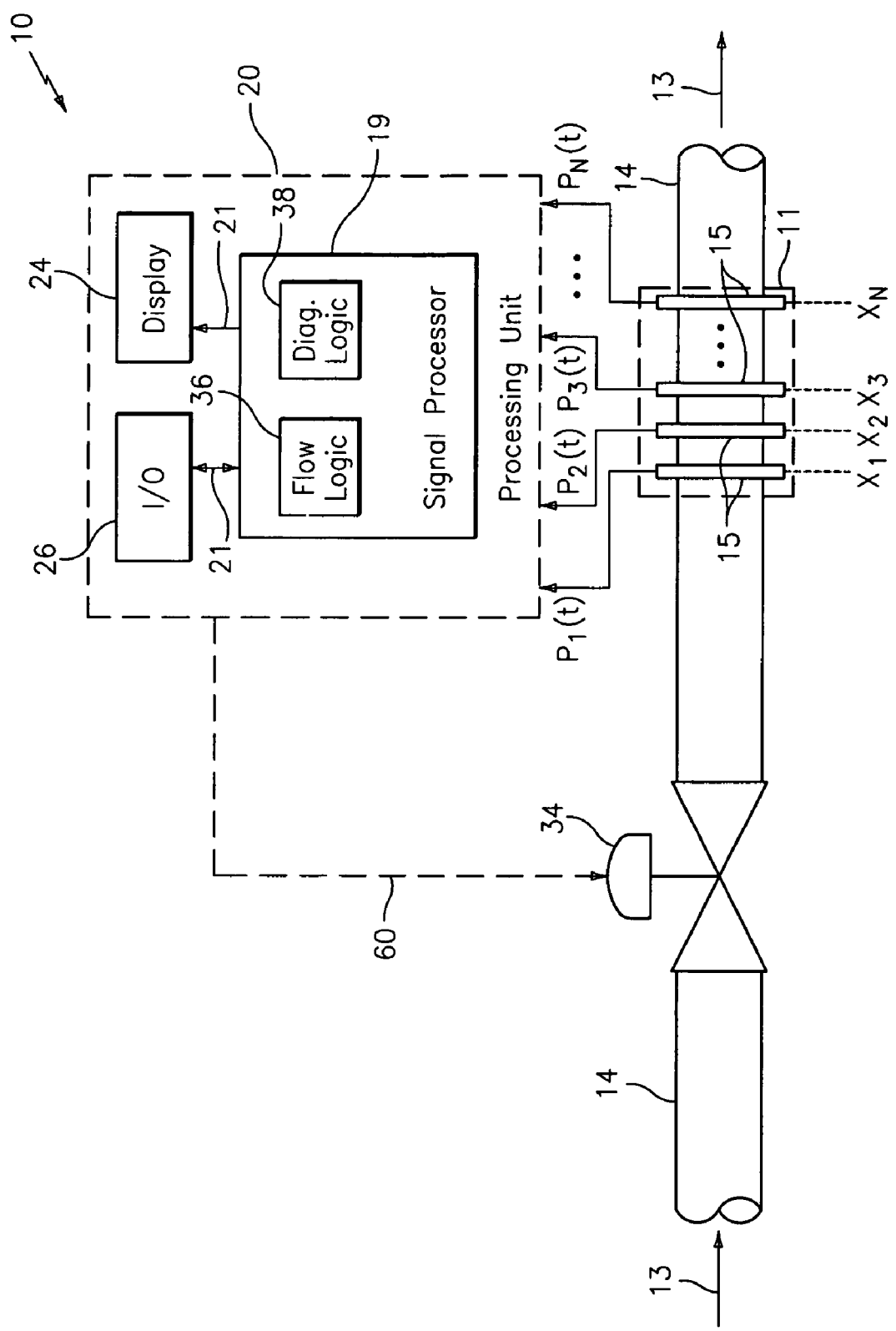
FIG. 4 is a schematic diagram of an apparatus for determining at least one parameter associated with a fluid flowing in the pipe, the apparatus including an array of piezocable based sensors, in accordance with an embodiment of the present invention.

Referring to FIG. 4, a spatial array of sensors 15 is shown generally at 11. The array 11 forms part of an apparatus 10 for measuring at least one parameter of the fluid 13. As described in U.S. patent application Ser. Nos. 10/007,749, 10/349,716, 10/376,427, which are all incorporated herein by reference, unsteady pressures along a pipe, as may be caused by one or both of acoustic waves propagating through the fluid within the pipe and/or pressure disturbances that connect with the fluid flowing in the pipe (e.g., turbulent eddies and vertical disturbances), contain useful information regarding parameters of the fluid and the flow process. The fluid 13 may be a single or multiphase fluid flowing through a duct, conduit or other form of pipe 14.

In the array 11, the sensors 15 are disposed at different axial locations $x_1 \ldots x_N$ along the pipe 14. Each of the sensors 15 provides a pressure signal P(t) indicative of unsteady pressure within the pipe 14 at a corresponding axial location $x_1 \ldots x_N$ of the pipe 14. A signal processor 19 receives the pressure signals $P_1(t) \ldots P_N(t)$ from the sensors 15 in the array 11, determines the parameter of the fluid 13 using the pressure signals $P_1(t) \ldots P_N(t)$, and outputs the parameter as a signal (parameter) 21.

While the array 11 is shown as including four sensors 15, it is contemplated that the array 11 may include two or more sensors 15, each providing a pressure signal P(t) indicative of unsteady pressure within the pipe 14 at a corresponding axial location X of the pipe 14. For example, the apparatus may include 2, 3, 4, 5, 6, 7, 8, 9, 10, 11, 12, 13, 14, 15, 16, 17, 18, 19, 20, 21, 22, 23, or 24 sensors 15. Generally, the fidelity of the measurement improves as the number of sensors 15 in the array increases. The degree of accuracy provided by the greater number of sensors 15 is offset by the increase in complexity and time for computing the desired output parameter 21 of the fluid 13. Therefore, the number of sensors 15 used is dependent at least on the degree of accuracy desired and the desired update rate of the output parameter 21 provided by the apparatus 10. Further, the number of sensors 15 used is dependent upon the coherency length of the unsteady pressure being measured. A greater number of sensors may require a longer aperture (i.e., array length) that is greater than the length of coherency of the signals being measured, which produces loss of coherence of the measured pressures.

The signals $P_1(t) \ldots P_N(t)$ provided by the sensors 15 in the array 11 are processed by the signal processor 19, which may be part of a larger processing unit 20. For example, the signal processor 19 may be a microprocessor and the processing unit 20 may be a personal computer or other general purpose computer. It is contemplated that the signal processor 19 may be any one or more signal processing devices for executing programmed instructions, such as one or more microprocessors or application specific integrated circuits (ASICS), and may include memory for storing programmed instructions, set points, parameters, and for buffering or otherwise storing data.

The pressure signals $P_1(t) \ldots P_N(t)$ provided by each respective sensor 15 are processed by the signal processor 19, which applies this data to flow logic 36 executed by the signal processor 19 to determine the one or more parameters 21 associated with the fluid 13, such as volumetric flow rate, mass flow rate, density, composition, entrained air, consistency, particle size, velocity, mach number, speed of sound propagating through the fluid, and/or other parameters of the fluid 13. The flow logic 36 is described in further detail hereinafter.

The signal processor 19 may also apply one or more of the pressure signals $P_1(t) \ldots P_N(t)$ and/or one or more parameters 21 from the flow logic 36 to diagnostic logic 38. Diagnostic logic 38 is executed by signal processor 19 to diagnose the health of any device 34 in the process flow that causes unsteady pressures to be generated in the section of the pipe 14 where the array 11 of sensors 15 are disposed. In FIG. 4, device 34 is depicted as a valve; however, it is contemplated that device 34 may be any machinery, component, or equipment, e.g. motor, fan, pump, generator, engine, gearbox, belt, drive, pulley, hanger, clamp, actuator, valve, meter, or the like. The signal processor 19 may output one or more parameters indicative of the health of the diagnosed device 34. The diagnostic logic 38 is described in further detail hereinafter.

The signal processor 19 may output the one or more parameters 21 to a display 24 or another input/output (I/O) device 26. The I/O device 26 also accepts user input parameters 48 as may be necessary for the flow logic 36 and diagnostic logic 38. The I/O device 26, display 24, and signal processor 19 unit may be mounted in a common housing, which may be attached to the array 11 by a flexible cable, wireless connection, or the like. The flexible cable may also be used to provide operating power from the processing unit 20 to the array 11 if necessary.

Figure 5:
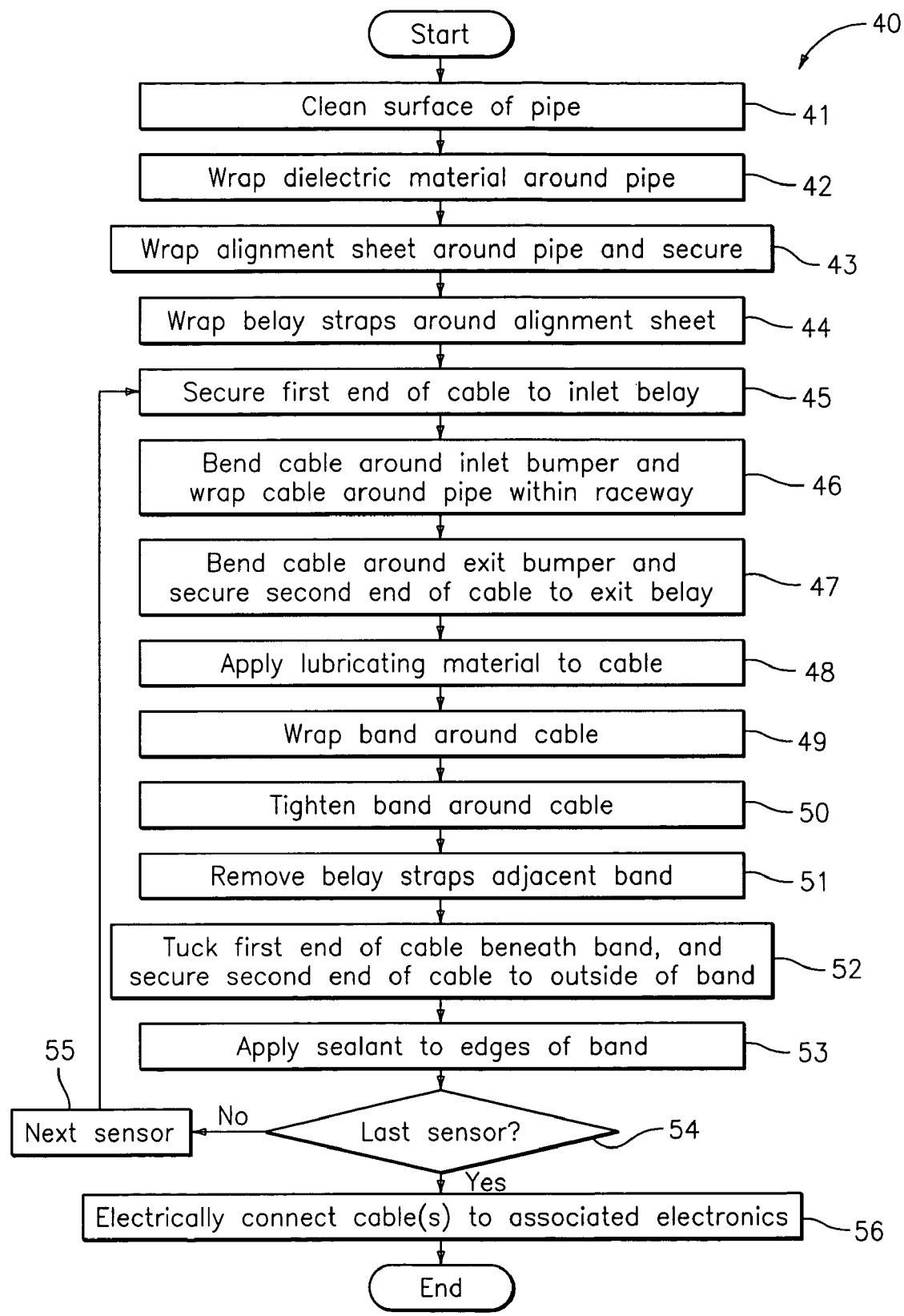
FIG. 5 is a flow chart depicting a method of installing piezocable based sensors, in accordance with an embodiment of the present invention.
Figure 6:
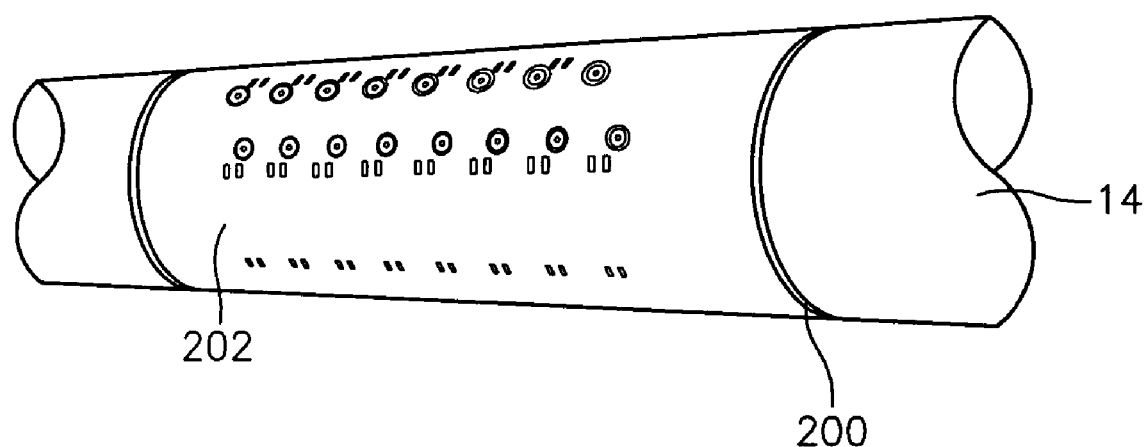
FIG. 6 is a perspective view of an alignment sheet and electrical insulating sheet wrapped around a pipe, in accordance with an embodiment of the present invention.

FIG. 5 depicts a method 40 of installing sensors 15 on the pipe 14, and referring to FIGS. 4-13, the method 40 is described. While the method 40 will be described with respect to the installation of an array 11 of sensors 15, it will be appreciated that the method 40 is also applicable to a single sensor 15. The installation begins with cleaning a surface of the section of pipe 14 onto which the sensors 15 are to be installed (block 41). This may include removing any debris on the pipe 14 to provide a smooth surface for receiving the sensors 15. A sheet or coating of electrically insulative material 200 is then applied around the pipe 14 (block 42), as shown in FIG. 6. For example, a sheet of Kapton® polymide, commercially available from E. I. du Pont de Nemours and Company of Wilmington, Del., may be used.

Next, an alignment sheet 202 is wrapped around the pipe 14, over the electrically insulative material 200, and secured in place (block 43). The alignment sheet 202 may be secured in place using springs or clamps extending between the ends of the alignment sheet 202. The electrically insulative material 200 extends continuously beneath the alignment sheet 202 and protrudes from the ends of the alignment sheet 202 for providing electrical insulation between the alignment sheet 202 and the pipe 14. While an alignment sheet 202 is described, one will appreciate that alignment sheet is not required in the installation of the sensors 15 but is beneficial in the ease and reliability of the installation of the cable 2 on the pipe 14. For instance, the sensors 15 may be simply wrapped the pipe 14 and may have an electrically insulative sheet 200 disposed between the sensors 15 and the pipe.

Figure 7:
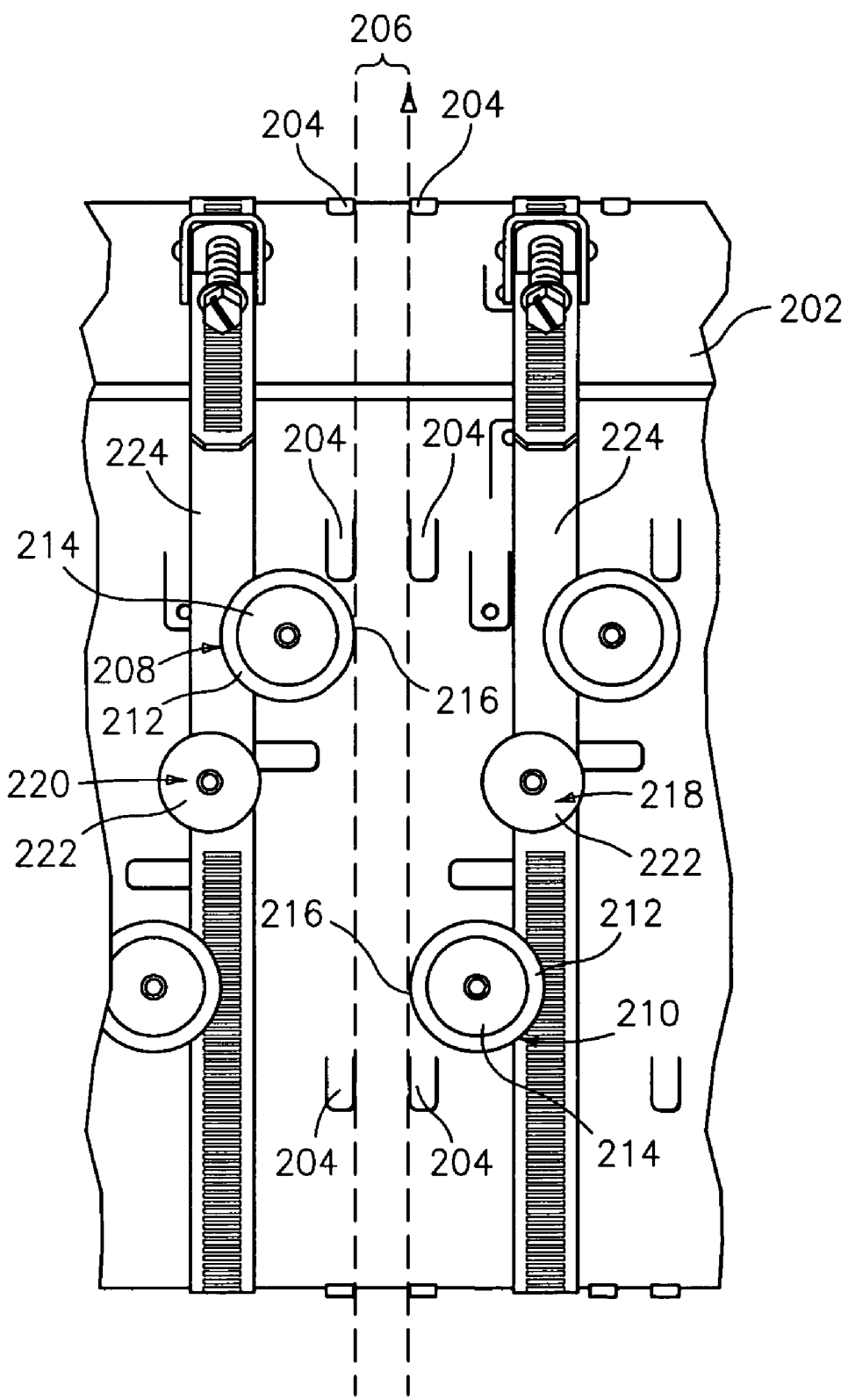
FIG. 7 is a plan view of a sensor raceway between cable inlet and exit bumpers and belays, in accordance with an embodiment of the present invention.

The alignment sheet 202 may be formed from a rigid material (e.g., metals, plastics, polymers etc.) that can be wrapped around the pipe 14. As best seen in FIG. 7, the alignment sheet 202 includes a plurality of spaced-apart tabs 204 protruding therefrom in a direction away from the pipe 14. The tabs 204 define sides of a raceway 206, which extends radially around the pipe 14 (substantially perpendicular to the pipe axis) for receiving the cable 2. One raceway 206 is provided for each sensor 15 to be installed. The tabs 204 maintain the desired sensor 15 location and spacing during assembly and operation. The width of each raceway 206 ensures that the desired width of the sensor 15 (i.e., the proper number of cable 2 turns) is attained during installation.

Fastened to the alignment sheet 202 on one side of each raceway 206 is a cable inlet bumper 208, and fastened to the alignment sheet 202 on an opposite side of each raceway 206 is a cable exit bumper 210. In the embodiment shown, the cable inlet and exit bumpers 208, 210 each include a lower disk 212 formed from a smooth, resilient material (e.g., plastic), and an upper disk 214 formed from a rigid material such as steel, both of which are secured to the alignment sheet 202 by a fastener (e.g., a rivet) disposed through the centers of the disks 212, 214. Each lower disk 212 has a radiused surface 216 formed thereon proximate the corresponding raceway 206. The upper disk 214 has a smaller diameter than the lower disk 212 and acts as a washer to provide rigidity to the lower disk 212. As will be described hereinafter, the radiused surface 216 provides a shoulder around which the cable 2 is bent to prevent damage to the cable 2 (e.g., cutting, breaking, kinking) during the installation process. It is contemplated that the inlet and exit bumpers 208, 210 may be any structure secured to the alignment sheet 202 that has a radiused surface 216 around which the cable 2 may be bent without damaging the cable 2.

If the alignment sheet 202 is formed of an electrically conductive material, the alignment sheet may be grounded to the amplifier ground to prevent capacitive coupling of electromagnetic signals propagating on the pipe 14 into the amplifier.

After the alignment sheet 202 has been wrapped around the pipe 14, cable inlet and exit belays 218, 220 are secured to the alignment sheet 202 on opposite sides of each raceway 206 (block 44). In the embodiment shown in FIG. 7, the cable inlet and exit belays 218, 220 each include a disk 222 of resilient material (e.g., plastic) fastened through its center to a belay strap 224. The belay strap 224 may be formed from a hose clamp, which can be tightened around the alignment sheet 202. As will be described hereinafter, the cable inlet and exit belays 218, 220 releasably retain the ends of the cable 2 to prevent damage to the cable 2 (e.g., cutting, breaking, kinking) during the installation process. It is contemplated that the inlet and exit belays 218, 220 may be any structure that releasably retains the ends of the cable 2 without damaging the cable 2.

Figure 8:
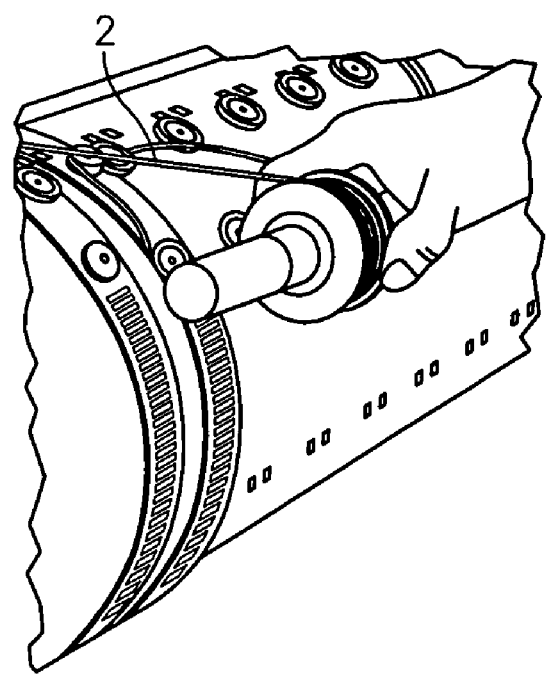
FIG. 8 is a perspective view of cable being wrapped around the pipe, in accordance with an embodiment of the present invention.
Figure 9:
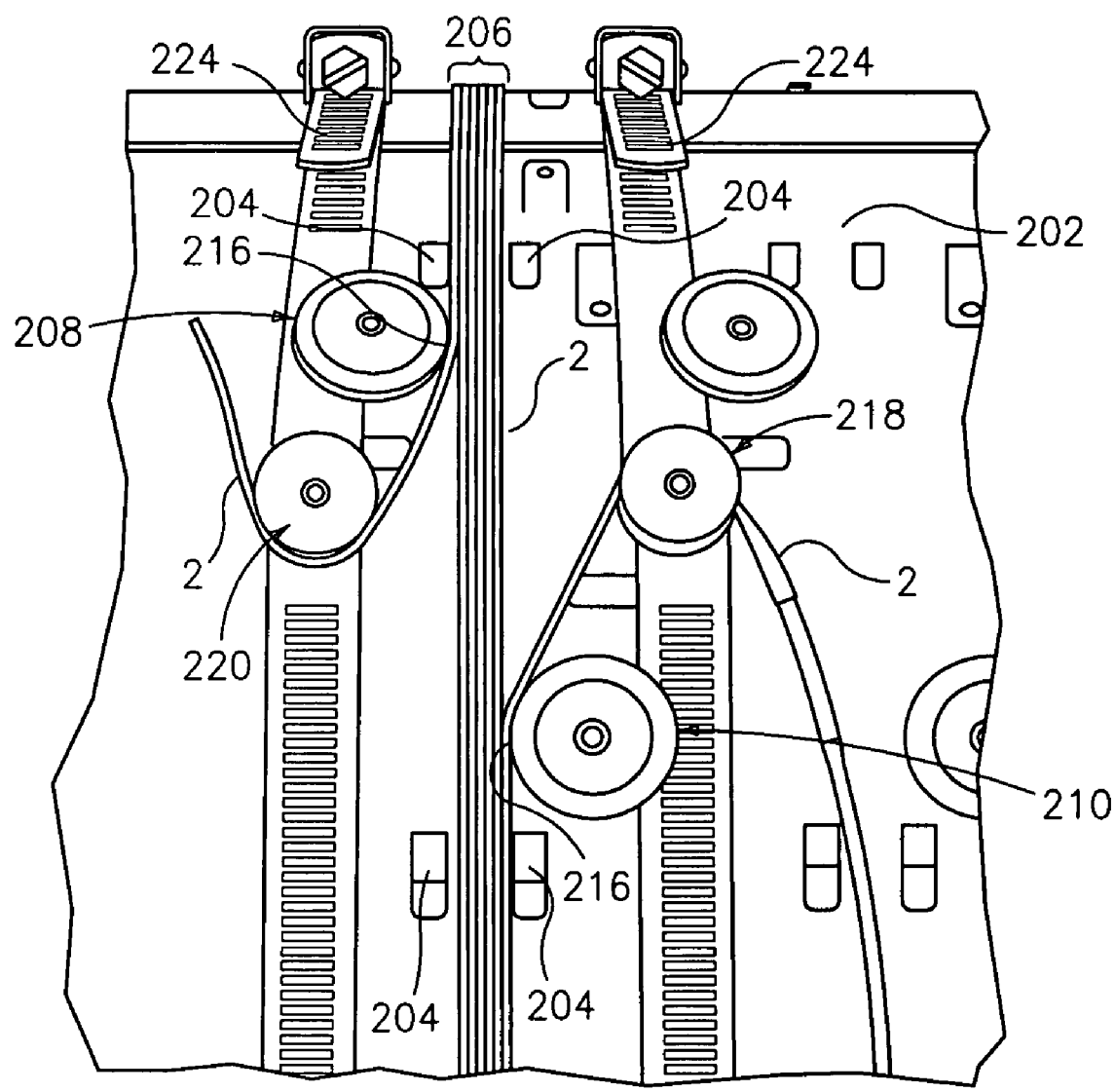
FIG. 9 is a plan view of cable wrapped around the pipe having its ends disposed in cable inlet and exit belays, in accordance with an embodiment of the present invention.

As shown in FIG. 9, after the cable inlet and exit belays 218, 220 are secured around the alignment sheet 202, one end of the cable 2 is wedged beneath the cable inlet belay 218, the cable 2 is bent around the radiused surface 216 of the cable inlet bumper 210, and the cable 2 is helically wrapped around the pipe 14 within the raceway 206 (block 46). As shown in FIG. 8, the cable 2 may be wound using a handheld spool, while keeping tension (e.g., about 5 pounds tension) on the cable 2.

After wrapping the cable 2 around the pipe a predetermined number of times, the cable 2 is bent around the cable exit bumper 208 and the end of the cable 2 is wedged beneath the cable exit belay 220 (block 47).

The end of the cable 2 secured by the cable exit belay 220 is insulated, with the inner and outer conductors 4, 6 (FIG. 1) of the cable 2 in electrical isolation from each other and from any electrically conductive object. The first and second conductors 4, 6 (FIG. 1) exposed at the end of the cable 2 secured by the cable inlet belay 218 may be coupled, by way of an industrial connector, to a non-piezoelectric cable, such as a low noise coaxial cable, to avoid triboelectrically generated noise in the signal from cable shaking and the like. As suggested hereinbefore, the present invention contemplates that the cable does not include an electrically insulated jacket 7. As such the outer conductor 6 and the alignment sheet 202 may both be grounded to the amplifier ground.

Figure 10:
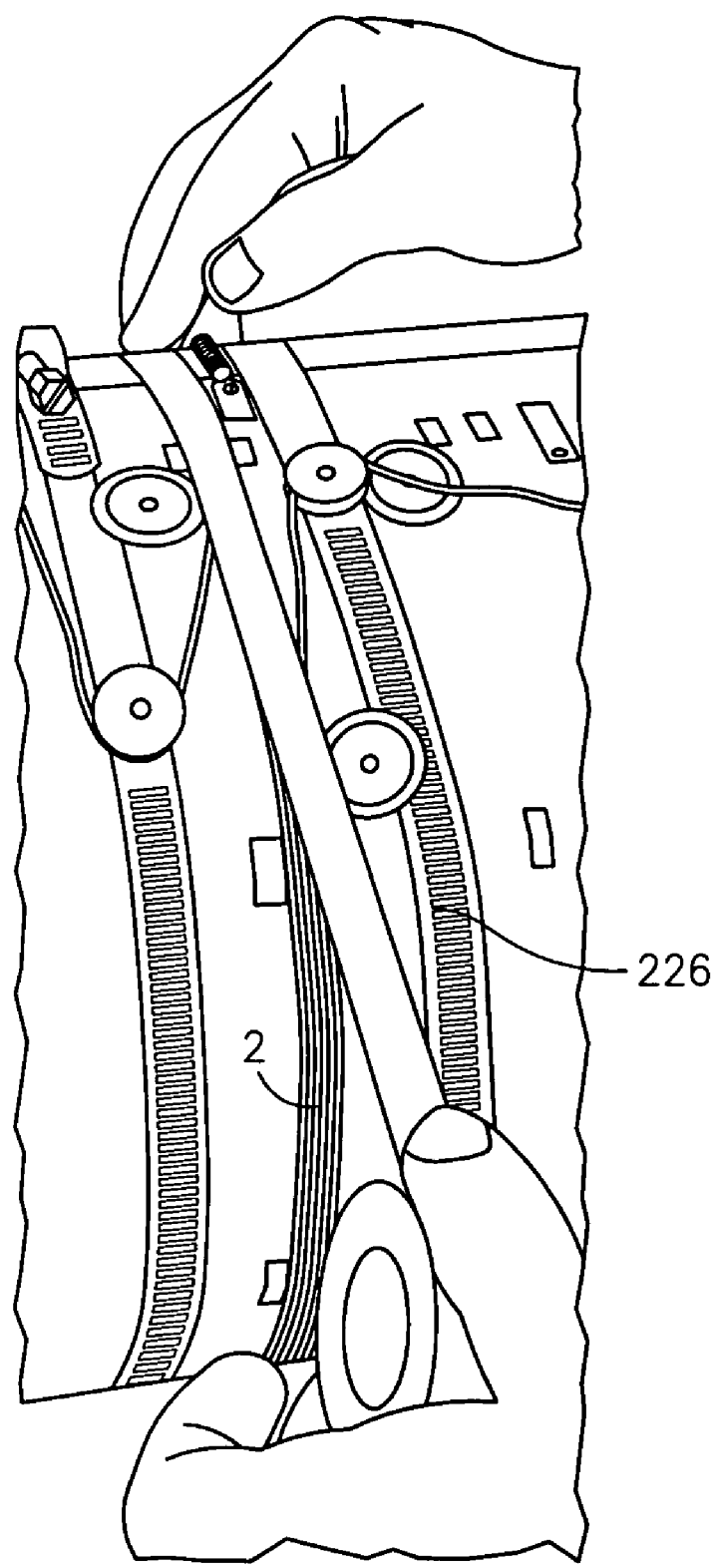
FIG. 10 is a perspective view of a lubricating material being applied to the cable, in accordance with an embodiment of the present invention.

After the cable 2 has been wrapped around the pipe 14, a lubricating material 226 may be applied around the cable 2 (block 48), as shown in FIG. 10. In the embodiment of FIG. 10, the lubricating material 226 is Teflon tape, which is wrapped around the cable 2 windings. It is contemplated that any convenient lubricating material may be wrapped or coated on the cable 2.

Figure 11:
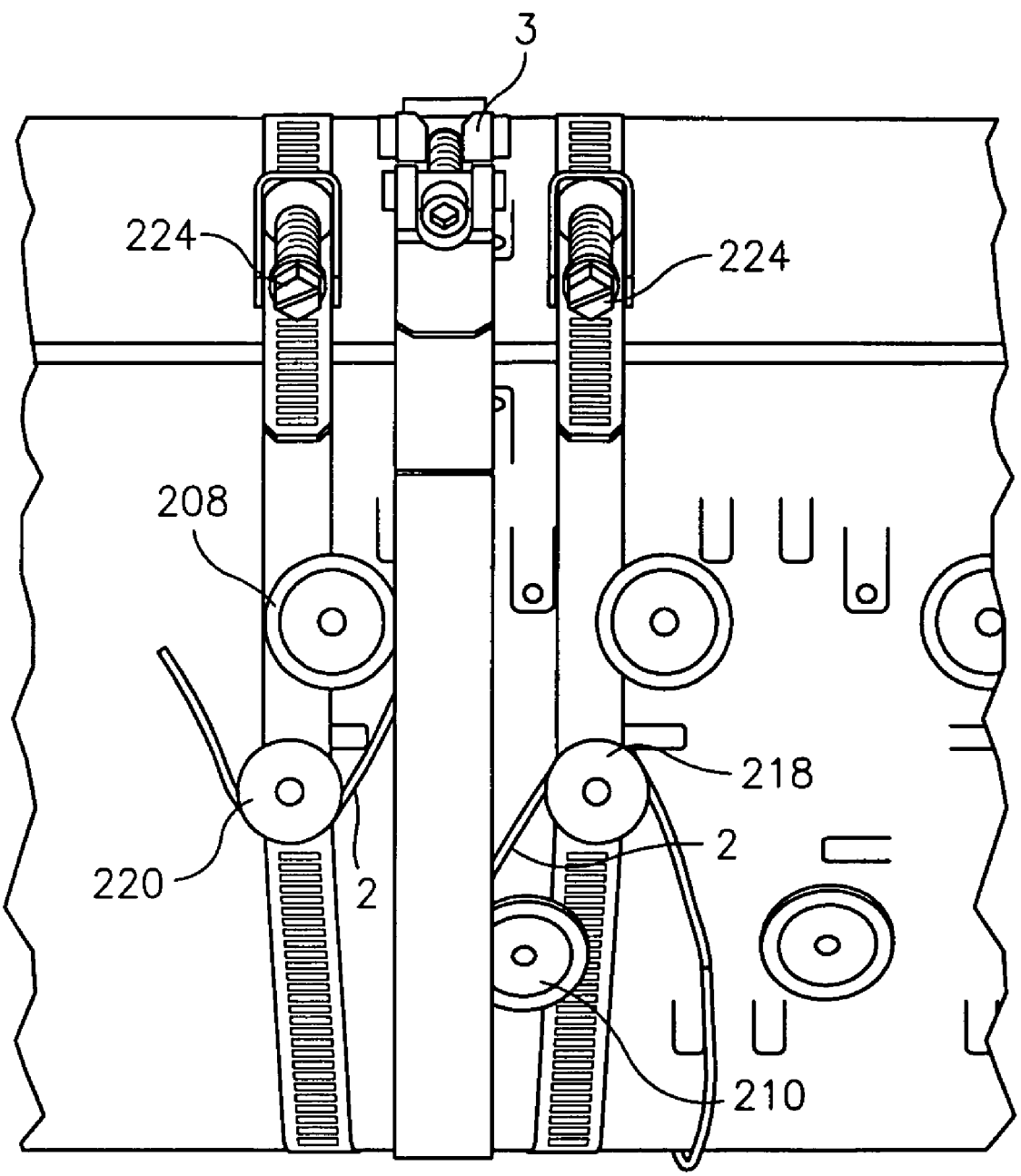
FIG. 11 is a plan view of the strap wrapped around the cable, in accordance with an embodiment of the present invention.

Next, the band 3 is wrapped around the cable 2 and tightened to compress (i.e., strain) the cable 2 against the pipe 14 (block 50), as shown in FIG. 11. The band 3 is formed from a relatively rigid material in comparison to the dielectric material 5 (FIG. 1). For example, the band 3 may be formed from metal, fiberglass, polymers, and the like. In the embodiment shown, the band 3 is a steel hose clamp, which may be torqued to a predetermined value (e.g., 20 inch-pounds). The lubricating material 226 (FIG. 10) prevents binding between the band 3 and cable 2. The band 3 may also be spring loaded (e.g., a spring loaded hose clamp) to insure good contact with the cable 2 in the presence of long term settling. The cable provides a greater signal amplitude, the stiffer the band 3 is. Conversely, the less stiff the band is, the smaller the amplitude of the signal provided by the cable 2.

While the sensor 15 includes a band 3 clamped around the cable 2 to compress the cable 2 toward the pipe 14, the present invention contemplates an embodiment that does not include a band. In this embodiment, the center conductor 4 provides the necessary compressive force on the piezoelectric material 5. This embodiment having no band 6, however, provide a signal having less amplitude because a lesser portion of the piezoelectric material 5 is strained in response to unsteady pressure (piezoelectric material disposed between the center conductor and the pipe).

Figure 12:
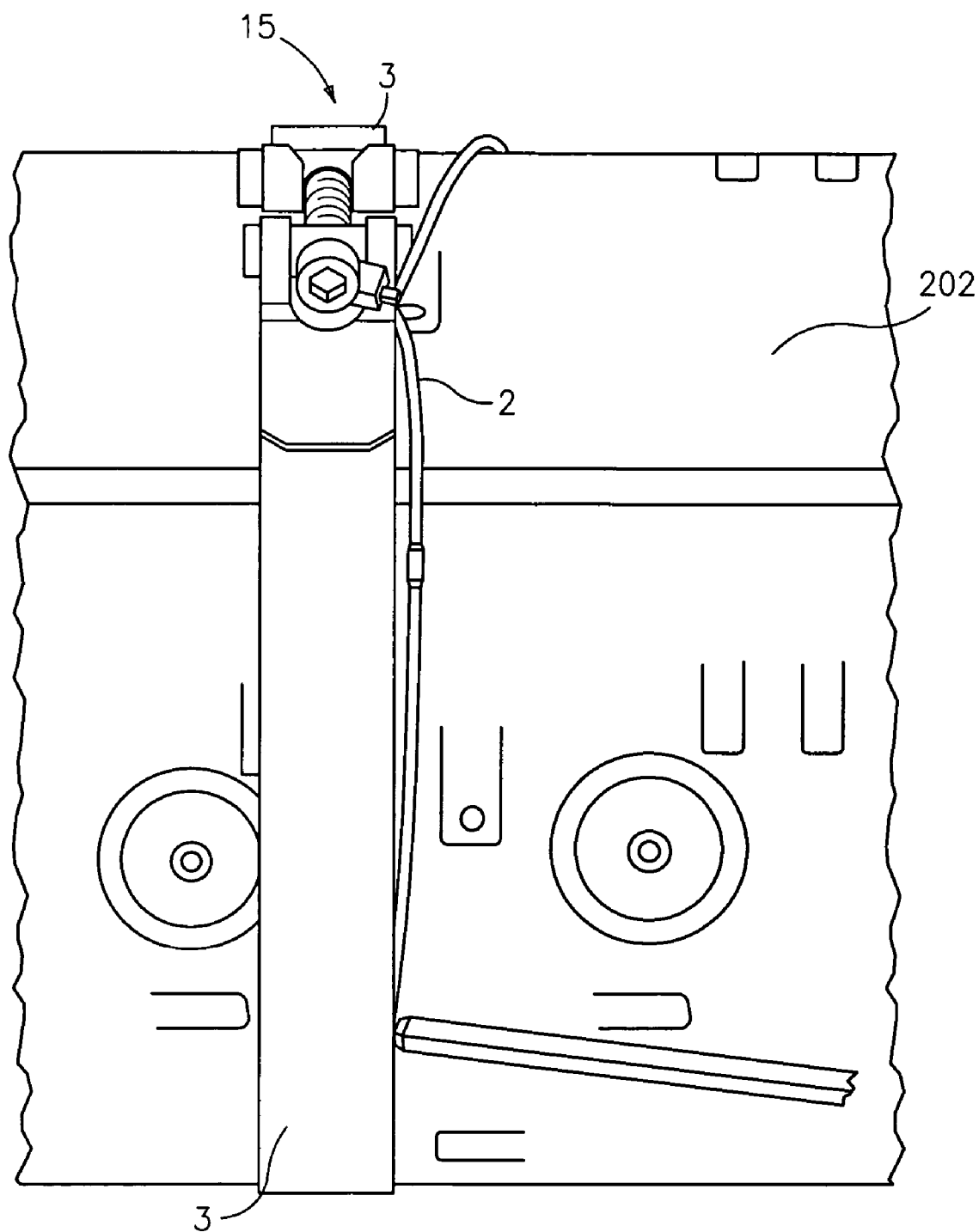
FIG. 12 is a plan view depicting one end of the cable secured to the strap, in accordance with an embodiment of the present invention.
Figure 13:
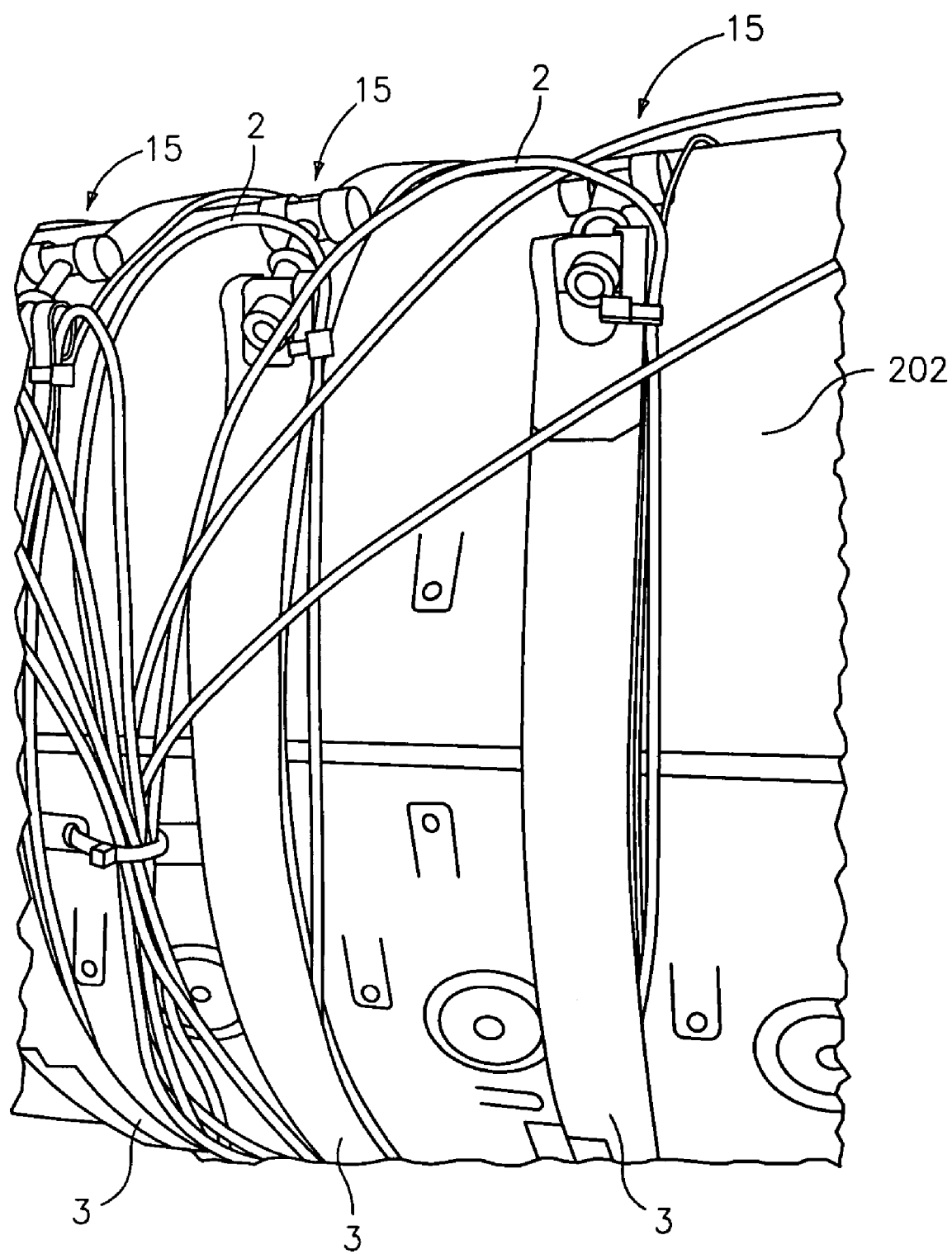
FIG. 13 depicts a plurality of cables bundled for electrical connection to associated electronics, in accordance with an embodiment of the present invention.

After the band 3 is tightened, the belay straps 224 adjacent the band 3 are removed (block 51), the insulated end of the cable 2 is tucked beneath the band 3, and the opposite (spliced) end of the cable 2 is mechanically secured to the band 3 (e.g., to a clamp portion of the band 3 or other convenient structure) (block 52), as shown in FIG. 12. A sealant may be applied along side edges of the band 3 to hold the cable 2 in place and prevent vibration of the cable 2 and band 3 (block 53).

Blocks 45-53 through are repeated for each sensor 15 in the array (blocks 54, 55). After all of the sensors 15 have been installed, the cables 2 (or non-piezoelectric cables spliced to the cables 2) from each of the sensors 15 are mechanically secured to a convenient structure, and the cables 2 (or non-piezoelectric cables spliced to the cables 2) are electrically connected to the processing unit 20 (FIG. 4) or to other associated electronics (e.g., a charge amplifier for impedance conversion of the output signals from the sensors 15) that are in turn coupled to the processing unit 20 (block 56).

One advantage of the present invention is that the piezoelectric-based cable sensor 15 and arrangement thereof may function at temperatures greater than that of piezoelectric sensors formed of piezoelectric sheet material. For example, the maximum operating temperature of the piezoelectric cable is between approximately 150° C. to 160° C., while the maximum operating temperature of piezoelectric sheet or strip is approximately 85° C. to 100° C. In addition, unlike the cable 2, the piezoelectric sheet 230 is attached to the pipe 14 or a strap (not shown) by an adhesive which may also limit the operating temperature of the sensor, which will be described in greater detail hereinafter.

Figure 14:
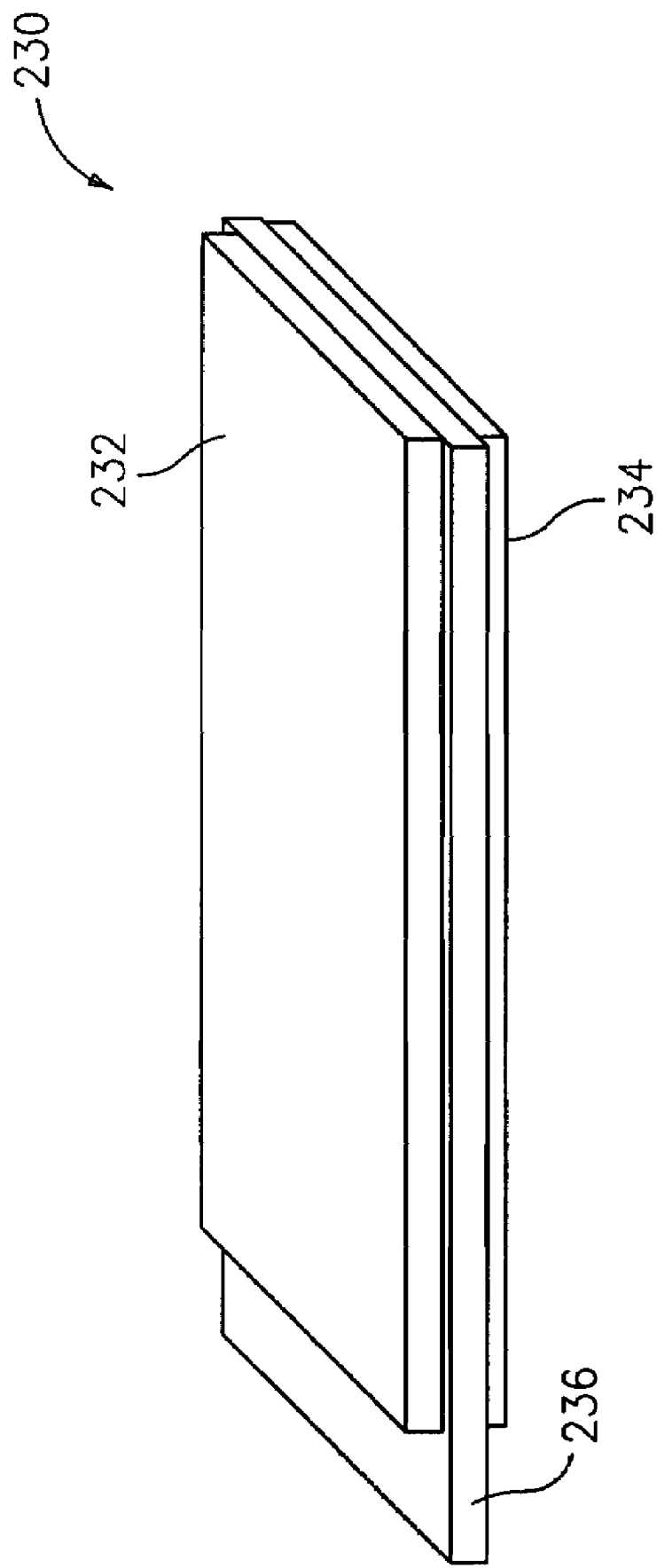
FIG. 14 is a prior art PVDF sheet or band.

One advantage of the present invention is that it eliminates the need for using an adhesive to affix the piezoelectric materials to the pipe 14 or to the inner and outer conductors 4, 6 (FIG. 1). For example, FIG. 14 shows a known PVDF sheet or band 230 that includes one electrode 232 adhered on oneside of PVDF material 236 and another electrode 234 adhered on another side of the PVDF material 236. The PVDF sheet 230 may also include an insulative material (not shown) disposed on either side of the electrodes 232 which may, in turn, be adhered to a pipe (not shown) or mounting strap (not shown).

While the PVDF sheet 230 works well for lower temperature applications, the use of adhesives to affix the piezoelectric material 236 (e.g., PVDF) to the electrodes 232, 234 and/or pipe may limit the temperatures under which the PVDF sheet 230 may be used. More specifically, PVDF material 236 is made piezoactive by stretching the material to orient the β (piezoactive) phase. High temperatures release the β phase orientation and shrink the PVDF material 236 along the stretch direction. Under lower temperatures, adhesives are effective in preventing the PVDF material 236 from shrinking. However, when certain high temperatures are reached, adhesives have been found to be unsuccessful at resisting shrinkage of the PVDF material 236, with a resulting drop in sensitivity of the PVDF sheet 230.

The geometry of the piezo-based cable 2 provides a more functionally stable sensor at higher temperature ranges than the PVDF sheets or strips attached to a pipe or band by an adhesive, which is susceptible to aging, humidity, high temperatures and interfaces with separate materials. Referring to FIG. 1, it has been found that the cable 2 used in the sensor 15 of the present invention "locks" piezoelectric material 5 in place between the inner and outer conductors 4, 6. While not wanting to be bound by theory, it is believed that the helical wrap of the piezoelectric material 5 around the inner conductor 4 prevents the piezoelectric material 5 from constricting beyond the diameter of the inner conductor 4 when exposes to high temperatures. Particularly, the axial symmetry of the center conductor having a round cross section provides a means for the helically wound PVDF (or other piezoelectric sheet material) to shrink onto the center conductor uniformly. Thus the temperature excursions "lock" the piezoelectric material 5 in place, preserving orientation of the beta phase, and providing long-term stability.

While the PVDF sheet 230 of FIG. 14 may be processed to make it less susceptible to these effects, such processing is costly and limited in effect. The sensor 15 of FIG. 1 is therefore less costly to implement. The cable 2 can be spooled off and cut to a desired length. The cable 2 does not require screen printed or otherwise adhered electrodes, which would have to be sized for a specific pipe diameter, and is therefore less expensive, more versatile and more readily available.

Figure 15:
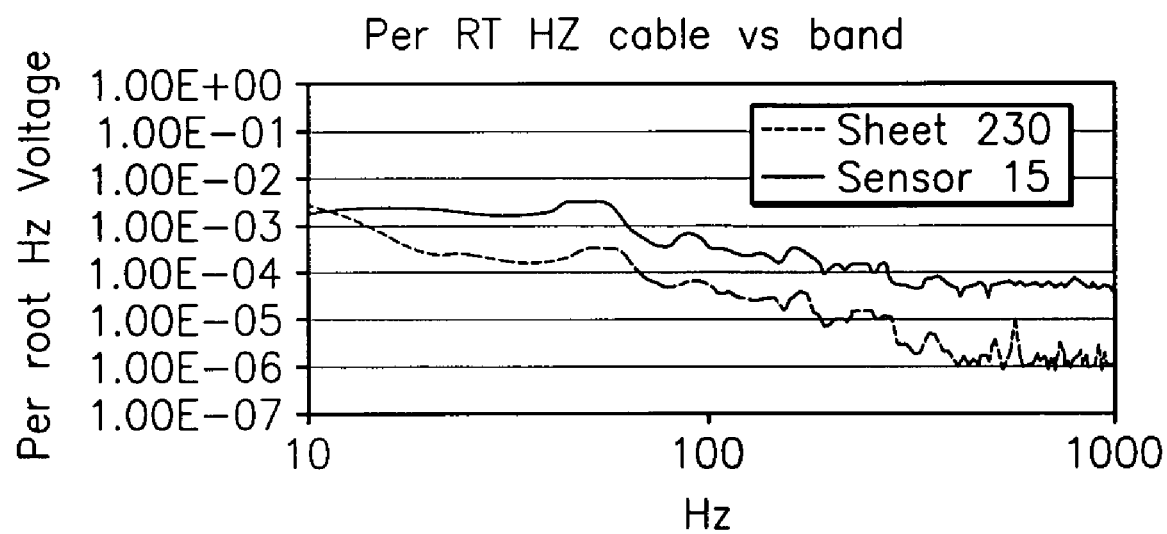
FIG. 15 is a per root Hz spectrum comparison between a PVDF sheet and the piezocable used in the piezocable based sensor of the present invention.

Furthermore, it has been found experimentally and analytically that approaches using a voltage amplifier and the PVDF sheet 230 of FIG. 14 adhered to a pipe are less sensitive, by a factor of at least 10, at measuring conduit dynamic pressures when compared to the sensor 15 of the present invention. For example, FIG. 15 shows a per root Hz spectrum comparison between the PVDF sheet 230 of FIG. 14 adhered around a pipe and a sensor 15 of the present invention including a 10 foot length of cable 2 wrapped in a tight helix and covered with a tight fittinghose clamp as outer band 3 type. As can be seen in FIG. 15, the sensor 15 of the present invention is an order of magnitude more sensitive at measuring dynamic pressures within an 8" pipe flowing water at 5 ft/sec.

While not wanting to be bound by theory, it is believed that the increased sensitivity of the sensor 15 can be explained by noting that, while both the PVDF sheet 230 of FIG. 14 and the cable 2 of FIG. 1 are subjected to longitudinal (i.e., stretching) strains caused by the expansion and contraction of the pipe, the cable 2 is also sensitive to radial strains. The radial strains result from the interference between the outer pipe wall and the radial stiffness of the inner conductor 4, which is further enhanced with the addition of the outer band 3.

Referring now to FIG. 16, an exploded perspective view of a housing 300 for the sensors 15 is shown. While the housing 300 is shown as covering the sensors 15, it is contemplated that the housing 300 may be used for any electrical device associated with the pipe 14. The housing 300 protects the electrical device from environmental conditions and potentially damaging contact. Advantageously, the housing 300 includes a sealing arrangement that makes the housing 300 particularly impervious to water spray and other precipitation.

The housing 300 includes a generally cylindrical shell 302, which extends coaxially around the pipe 14. The shell 302 is formed by two shell half-sections 304, which may be secured together by fasteners disposed along flanges 306 formed on the shell half-sections 304. The shell 302 has an inside diameter greater than the outside diameter of the pipe 14 so that an annular chamber 310 is formed between the outer surface of the pipe 14 and the shell 302 when the shell is installed around the pipe 14. The sensors 15 or other electrical devices may be housed in the annular chamber 310.

The housing 300 may also include a compartment 308 formed integral thereto, which may be used to house electronics 312 associated with the electrical devices in the annular chamber 310. For example, the compartment 308 may house an amplifier associated with the sensors 15. The compartment 308 includes a removable panel 314 to allow easy access to the electronics 312.

The shell 302 includes end walls 316 which extend radially inward and terminate at the surface of the pipe 14. Extending axially outward from the end walls 316 are flanges 318, which circumscribe the pipe 14 while being spaced apart therefrom. When the half-sections 304 are joined around the pipe 14, the flanges 318, a portion of the end walls 316 proximate the pipe 14, and the outer surface of the pipe 14 form annular chambers 320 at each end of the shell 302.

Housing 200 further includes gland rings 322 disposed at each end of the shell 302. Each gland ring 322 includes a short cylindrical portion 324 that extends coaxially with the pipe 14, and a flange portion 326 that extends radially from the cylindrical portion 324. Each gland ring 322 is formed from sections, which are fastened together to form a ring around the pipe 14.

Figure 18:
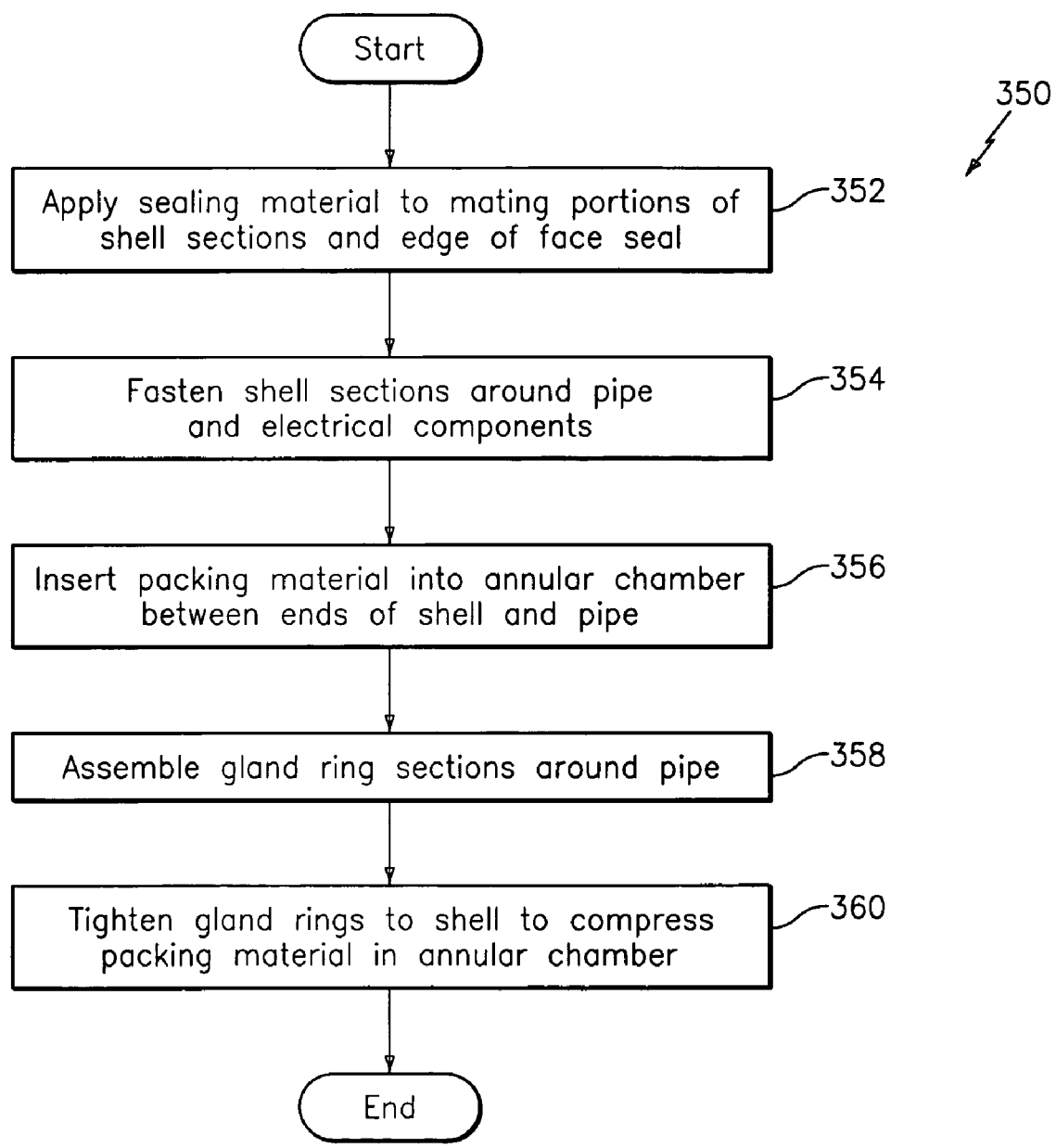
FIG. 18 is a flow chart depicting a method of installing the housing of FIG. 17.

Referring now to FIGS. 16-18, a method 350 of installing the housing 300 will be described. Installation begins by applying sealing material (e.g., a Teflon gasket) to the entire inner edge of each shell half-section 304, including mating portions of the shell half-sections 304 (e.g., flanges 306 disposed on the shell half-sections) and the end surfaces of the end walls 316 (block 352). This sealing material provides a primary seal between the outer diameter of the pipe 14 and the end walls 316 and between the mating portions of the shell 302.

The shell sections 304 are then fastened around the pipe 14 and the electrical components (e.g., sensors 15) (block 354). Next, a ring of packing material 330 (e.g., a Teflon gasket) is wrapped around the pipe 14 and slid into the annular chambers 320 formed at the ends of the shell 302 (block 356). With the packing material installed, the gland rings 322 are assembled around the pipe 14 (block 358), and the cylindrical portion 324 of each gland ring 322 is disposed in its associated annular chamber 320 against the packing material 330. Bolts 332 are fastened between the flanges 326 on the gland rings 322 and the shell 302, and the bolts 332 are tightened to draw the gland rings 322 axially towards the shell 302 (block 360). Tightening the gland ring 322 compresses the packing material within the annular chambers 320, which causes the packing material therein to expand radially and seal the housing 300 to the pipe 14 as shown in FIG. 17. The sealing arrangement shown in FIG. 17 protects the electrical devices in the annular chamber 310 from environmental conditions, particularly water spray and other precipitation. The sealing arrangement at the ends of the housing 300 provides a tight seal that can compensate for variations in pipe 14 diameter and for manufacturing tolerances in the construction of the shell 302.

Diagnostic Logic

Figure 19:
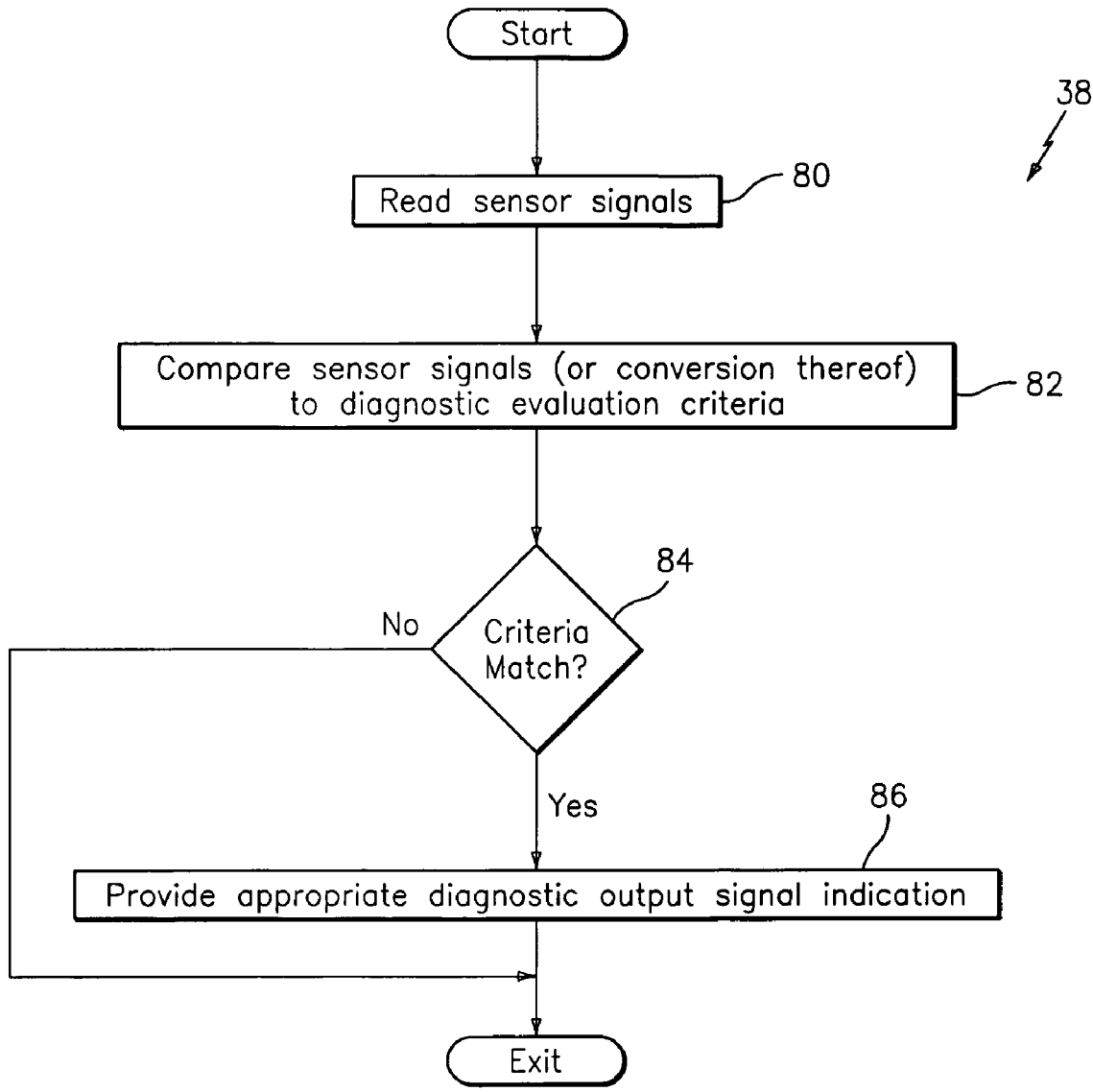
FIG. 19 is a block diagram of a diagnostic logic used in the apparatus of the present invention.

Referring to FIG. 19 the diagnostic logic 38 measures the sensor input signals (or evaluation input signals), which may include one or more of the signals $P_1(t), P_2(t), P_3(t), \ldots P_N(t)$ and the parameters 21, at a step 80. Next, the diagnostic logic 38 compares the evaluation input signals to a diagnostic evaluation criteria at a step 82, discussed hereinafter. Then, a step 84 checks if there is a match, and if so, a step 86 provides a diagnostic signal indicative of the diagnostic condition that has been detected and may also provide information identifying the diagnosed device. The diagnostic signal may be output as a parameter 21.

Where the evaluation input signal is a parameter 21, as may be output from the flow logic 36, the diagnostic evaluation criteria may be based on a threshold value of the flow signal 24. For example, the threshold value may be indicative of a maximum or minimum sound speed, mach number, consistency, composition, entrained air, density, mass flow rate, volumetric flow rate, or the like. If there is not a criteria match in step 84, the diagnostic logic 38 exits.

Where the evaluation input signal includes one or more signals $P_1(t), P_2(t), P_3(t), \ldots P_N(t)$, the diagnostic evaluation criteria may be a threshold (maximum or minimum) pressure. Alternatively, the diagnostic evaluation criteria may be based on an acoustic signature, or a convective property (i.e., a property that propagates or converts with the flow). For example, the diagnostic logic 38 may monitor the acoustic signature of any upstream or downstream device (e.g., motor, fan, pump, generator, engine, gear box, belt drive, pulley, hanger, clamp, actuator, valve, meter, or other machinery, equipment or component). Further, the data from the array 11 may be processed in any domain, including the frequency/spatial domain, the temporal/spatial domain, the temporal/wave-number domain, or the wave-number/frequency (k-ω) domain or other domain, or any combination of one or more of the above. As such, any known array processing technique in any of these or other related domains may be used if desired.

For example, for three unsteady pressure signals, the equations in the frequency/spatial domain equation would be:

$$P(x,\omega) = Ae^{-ik_r x} + Be^{+ik_l x};$$

the temporal/spatial domain would be:

$$P(x,t) = (Ae^{-ik_r x} + Be^{+ik_l x})e^{i\omega t};$$

and the k-ω domain (taking the spatial Fourier transform) would be:

$$P(k,\omega) = \frac{1}{2\pi}\int_{-\infty}^{+\infty} P(x,\omega)e^{ikx}\,dx = A(\omega)\delta\!\left(k - \frac{\omega}{a}\right) + B(\omega)\delta\!\left(k + \frac{\omega}{a}\right)$$

where k is the wave number, a is the speed of sound of the material, x is the location along the pipe, ω is frequency (in rad/sec, where ω=2πf), and δ is the Dirac delta function, which shows a spatial/temporal mapping of the acoustic field in the k-ω plane.

Any technique known in the art for using a spatial (or phased) array of sensors to determine the acoustic or convective fields, beam forming, or other signal processing techniques, may be used to provide an input evaluation signal to be compared to the diagnostic evaluation criteria.

Flow Logic

Velocity Processing

Figure 20:
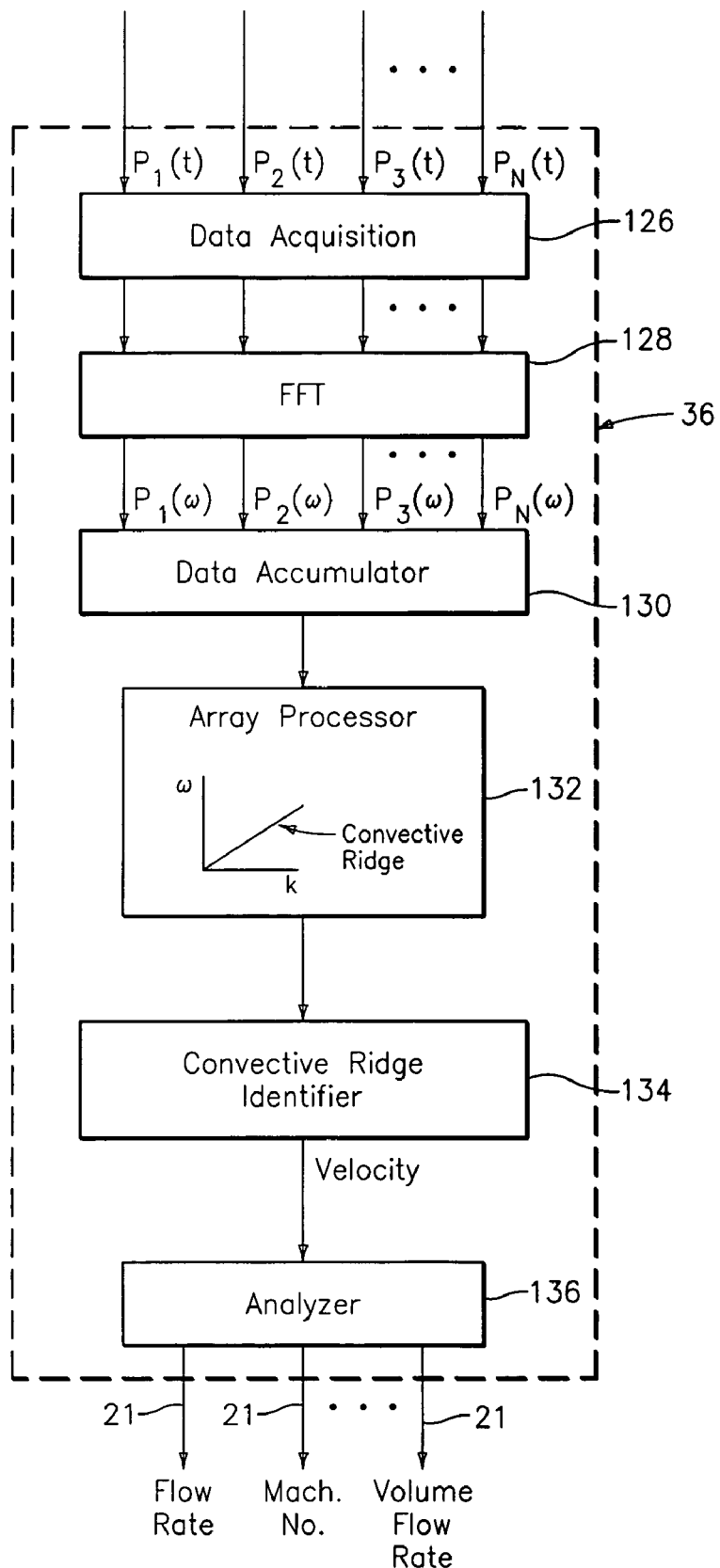
FIG. 20 is a block diagram of a first embodiment of a flow logic used in the apparatus of the present invention.
Figure 21:
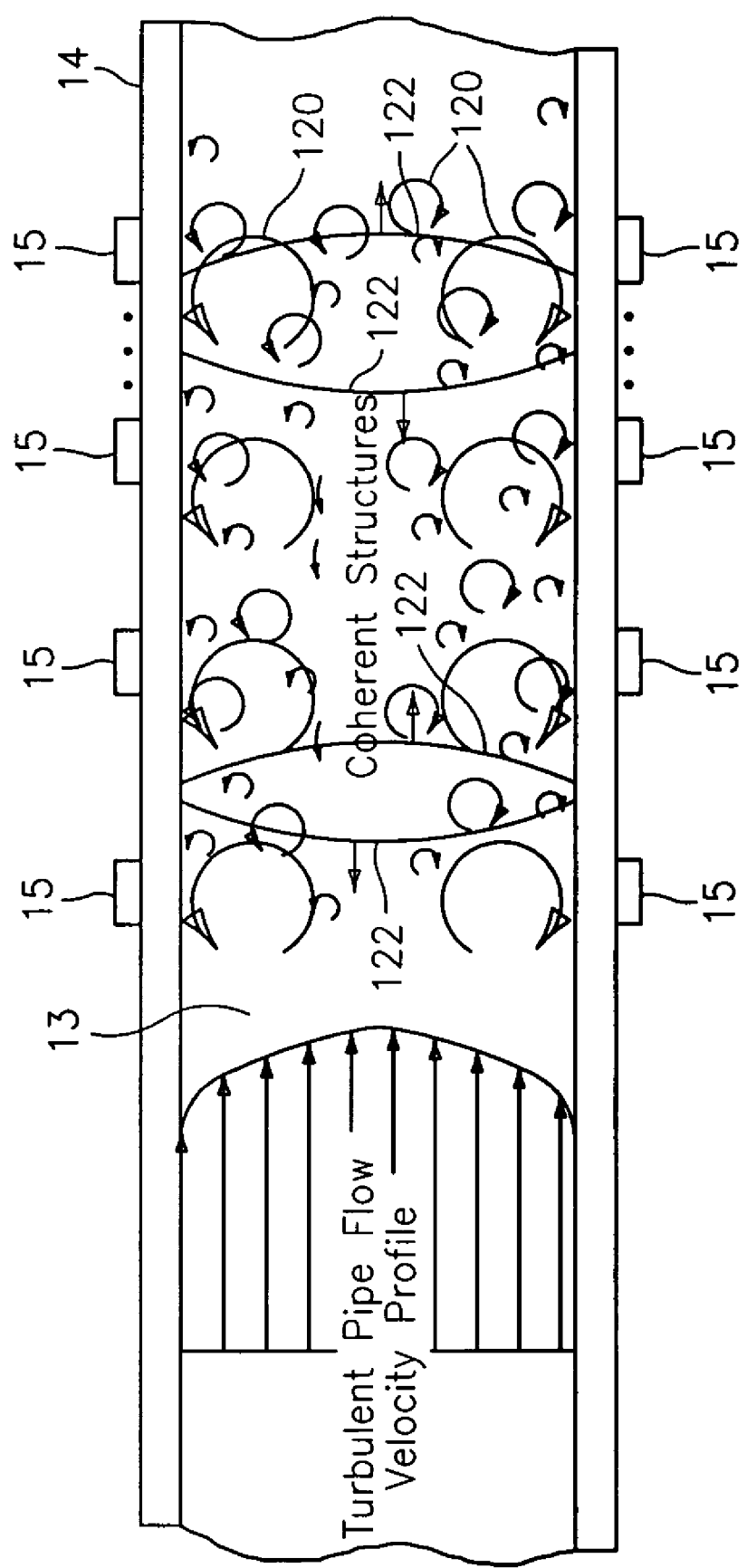
FIG. 21 is a cross-sectional view of a pipe having coherent structures therein, in accordance with an embodiment of the present invention.

Referring to FIG. 20, an example of flow logic 36 is shown. As previously described, the array 11 of at least two sensors 15 located at two locations $x_1$, $x_2$ axially along the pipe 14 sense respective stochastic signals propagating between the sensors 15 within the pipe 14 at their respective locations. Each sensor 15 provides a signal indicating an unsteady pressure at the location of each sensor 15, at each instant in a series of sampling instants. One will appreciate that the array 11 may include more than two sensors 15 distributed at locations $x_1 \ldots x_N$. The pressure generated by the convective pressure disturbances (e.g., eddies 120, see FIG. 21) may be measured through strained-based sensors 15 and/or pressure sensors 15. The sensors 15 provide analog pressure time-varying signals $P_1(t), P_2(t), P_3(t) \ldots P_N(t)$ to the signal processor 19, which in turn applies these signals $P_1(t), P_2(t), P_3(t), \ldots P_N(t)$ to the flow logic 36.

The flow logic 36 processes the signals $P_1(t), P_2(t), P_3(t), \ldots P_N(t)$ to first provide output signals (parameters) 21 indicative of the pressure disturbances that connect with the fluid (process flow) 13, and subsequently, provide output signals (parameters) 21 in response to pressure disturbances generated by convective waves propagating through the fluid 13, such as velocity, Mach number and volumetric flow rate of the process flow 13.

The signal processor 19 includes data acquisition unit 126 (e.g., A/D converter) that converts the analog signals $P_1(t) \ldots P_N(t)$ to respective digital signals and provides the digital signals $P_1(t) \ldots P_N(t)$ to FFT logic 128. The FFT logic 128 calculates the Fourier transform of the digitized time-based input signals $P_1(t) \ldots P_N(t)$ and provides complex frequency domain (or frequency based) signals $P_1(\omega), P_2(\omega), P_3(\omega), \ldots P_N(\omega)$ indicative of the frequency content of t input signals. Instead of FFT's, any other technique for obtaining the frequency domain characteristics of the signals $P_1(t)$-$P_N(t)$, may be used. For example, the cross-spectral density and the power spectral density may be used to form a frequency domain transfer functions (or frequency response or ratios) discussed hereinafter.

One technique of determining the convection velocity of the turbulent eddies 120 within the process flow 13 is by characterizing a convective ridge of the resulting unsteady pressures using an array of sensors or other beam forming techniques, similar to that described in U.S. Patent Application, Serial No. and U.S. patent application, Ser. No.

09/729,994, filed Dec. 4, 200, now U.S. Pat. No. 6,609,069, which are incorporated herein by reference.

A data accumulator 130 accumulates the frequency signals $P_1(\omega)$-$P_N(\omega)$ over a sampling interval, and provides the data to an array processor 132, which performs a spatial-temporal (two-dimensional) transform of the sensor data, from the xt domain to the k-ω domain, and then calculates the power in the k-ω plane, as represented by a k-ω plot.

The array processor 132 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where λ is the wavelength of a spectral component, and corresponding angular frequencies given by $\omega=2\pi\nu$.

The prior art teaches many algorithms of use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine flow rate, i.e. that the signals caused by a stochastic parameter connecting with a flow are time stationary and have a coherence length long enough that it is practical to locate sensor units apart from each other and yet still be within the coherence length.

Convective characteristics or parameters have a dispersion relationship that can be approximated by the straight-line equation, $$k=\omega/u,$$

where u is the convection velocity (flow velocity). A plot of k-ω pairs obtained from a spectral analysis of sensor samples associated with convective parameters portrayed so that the energy of the disturbance spectrally corresponding to pairings that might be described as a substantially straight ridge, a ridge that in turbulent boundary layer theory is called a convective ridge. What is being sensed are not discrete events of turbulent eddies, but rather a continuum of possibly overlapping events forming a temporally stationary, essentially white process over the frequency range of interest. In other words, the convective eddies 120 is distributed over a range of length scales and hence temporal frequencies.

To calculate the power in the k-ω plane, as represented by a k-ω plot (see FIG. 22) of either the signals, the array processor 132 determines the wavelength and so the (spatial) wavenumber k, and also the (temporal) frequency and so the angular frequency ω, of various of the spectral components of the stochastic parameter. There are numerous algorithms available in the public domain to perform the spatial/temporal decomposition of arrays of sensors 15.

The present invention may use temporal and spatial filtering to precondition the signals to effectively filter out the common mode characteristics $P_{common\ mode}$ and other long wavelength (compared to the sensor spacing) characteristics in the pipe 14 by differencing adjacent sensors 15 and retain a substantial portion of the stochastic parameter associated with the flow field and any other short wavelength (compared to the sensor spacing) low frequency stochastic parameters.

Figure 22:
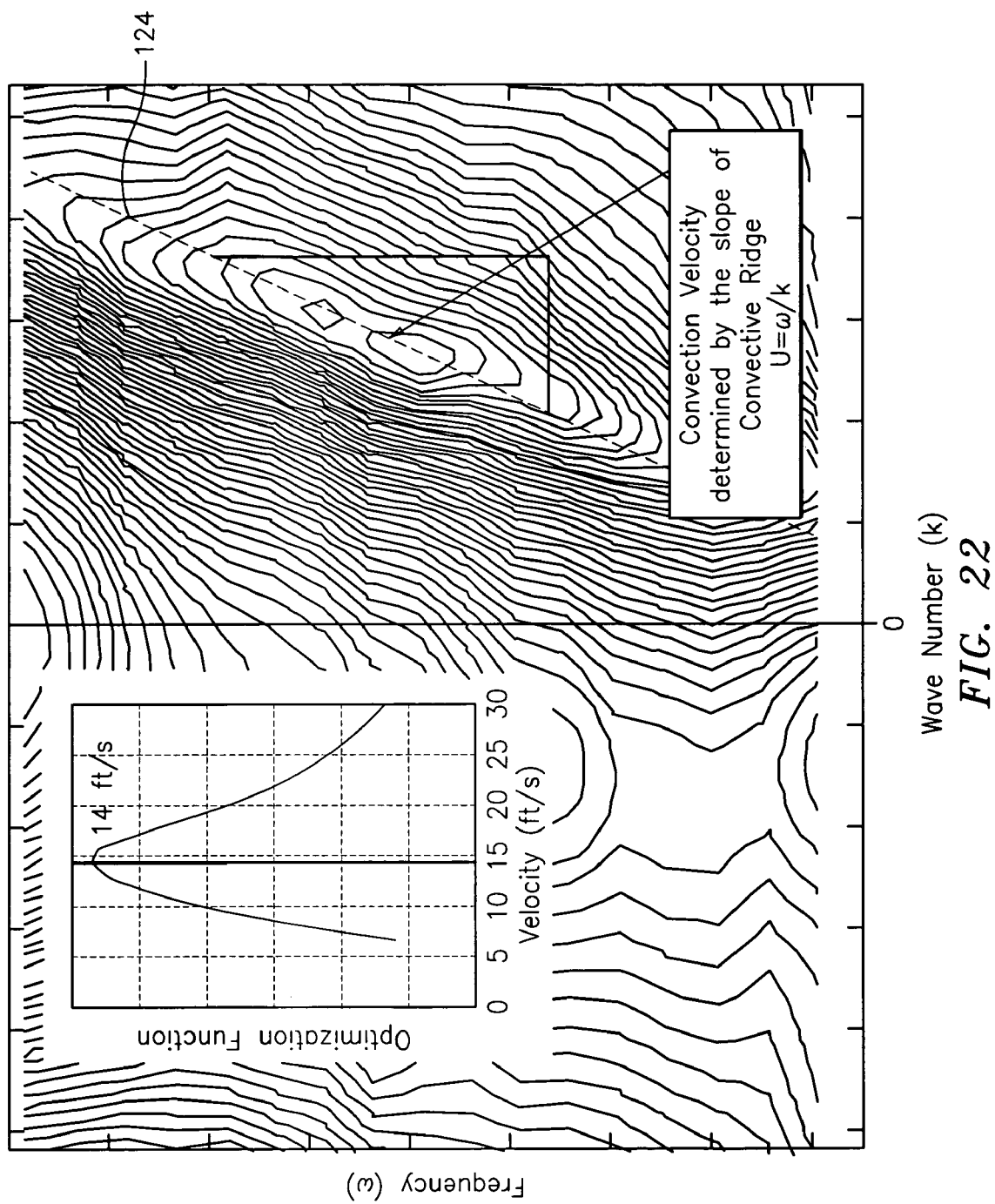
FIG. 22 a kω plot of data processed from an apparatus embodying the present invention that illustrates slope of the convective ridge, and a plot of the optimization function of the convective ridge, in accordance with an embodiment of the present invention.

In the case of suitable turbulent eddies 120 (see FIG. 21) being present, the power in the k-ω plane shown in a k-ω plot of FIG. 22 shows a convective ridge 124. The convective ridge represents the concentration of a stochastic parameter that converts with the flow and is a mathematical manifestation of the relationship between the spatial variations and temporal variations described above. Such a plot will indicate a tendency for k-ω pairs to appear more or less along a line 124 with some slope, the slope indicating the flow velocity.

Once the power in the k-ω plane is determined, a convective ridge identifier 134 uses one or another feature extraction method to determine the location and orientation (slope) of any convective ridge 124 present in the k-ω plane. In one embodiment, a so-called slant stacking method is used, a method in which the accumulated frequency of k-ω pairs in the k-ω plot along different rays emanating from the origin are compared, each different ray being associated with a different trial convection velocity (in that the slope of a ray is assumed to be the flow velocity or correlated to the flow velocity in a known way). The convective ridge identifier 134 provides information about the different trial convection velocities, information referred to generally as convective ridge information.

The analyzer 136 examines the convective ridge information including the convective ridge orientation (slope). Assuming the straight-line dispersion relation given by $k=\omega/u$, the analyzer 136 determines the flow velocity, Mach number and/or volumetric flow, which are output as parameters 21. The volumetric flow is determined by multiplying the cross-sectional area of the inside of the pipe with the velocity of the process flow.

Some or all of the functions within the flow logic 36 may be implemented in software (using a microprocessor or computer) and/or firmware, or may be implemented using analog and/or digital hardware, having sufficient memory, interfaces, and capacity to perform the functions described herein.

Speed of Sound (SOS) Processing

Figure 23:
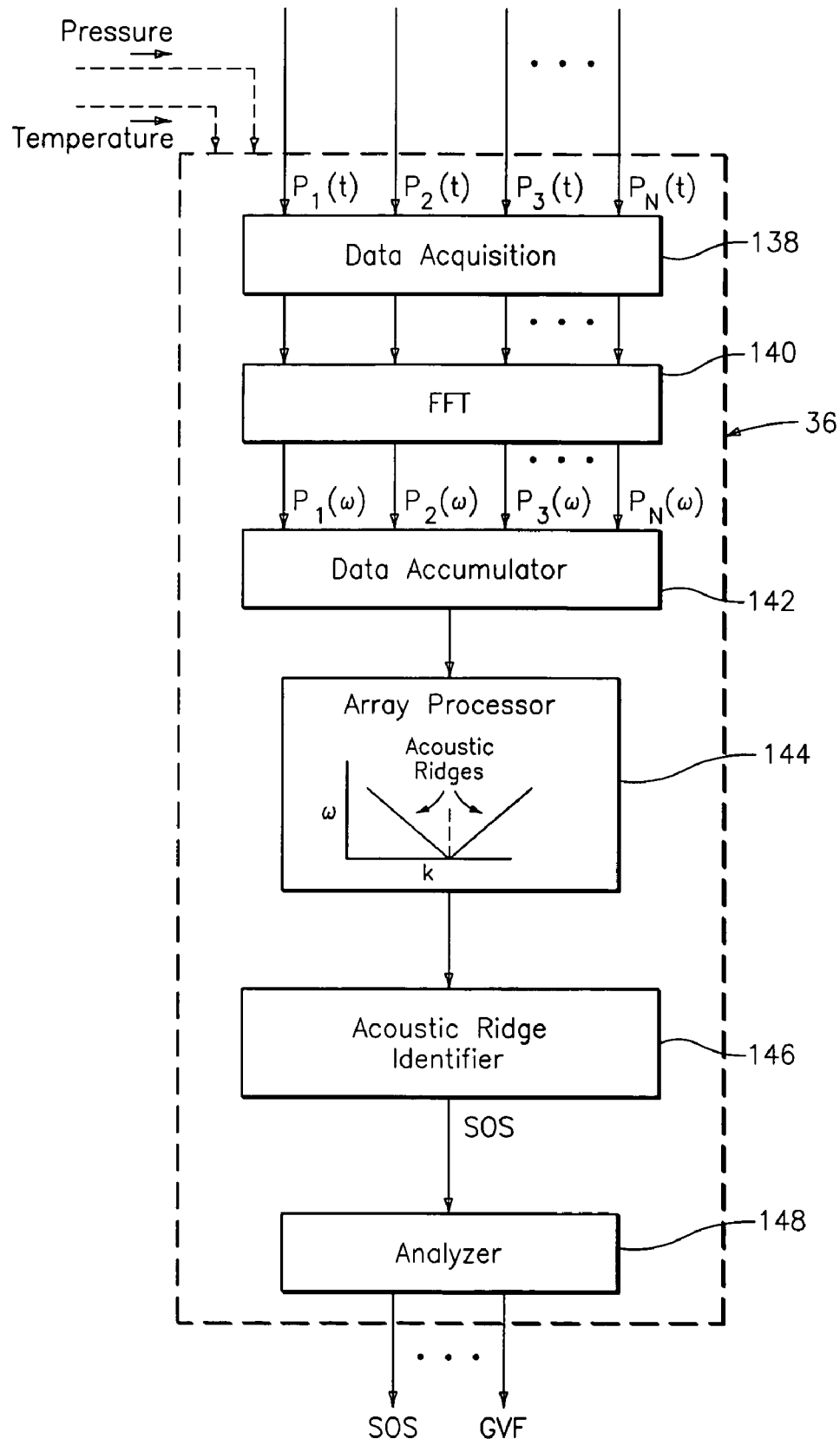
FIG. 23 is a block diagram of a second embodiment of a flow logic used in the apparatus of the present invention.

Referring to FIG. 23, another example of flow logic 36 is shown. While the examples of FIG. 20 and FIG. 23 are shown separately, it is contemplated that the flow logic 36 may perform all of the functions described with reference to FIG. 20 and FIG. 23. As previously described, the array 11 of at least two sensors 15 located at two at least two locations $x_1$, $x_2$ axially along the pipe 14 sense respective stochastic signals propagating between the sensors within the pipe at their respective locations. Each sensor 15 provides a signal indicating an unsteady pressure at the location of each sensor 15, at each instant in a series of sampling instants. One will appreciate that the sensor array 11 may include more than two pressure sensors 15 distributed at locations $X_1 \ldots x_N$. The pressure generated by the acoustic pressure disturbances (e.g., acoustic waves 122, see FIG. 21) may be measured through strained-based sensors and/or pressure sensors. The sensors 15 provide analog pressure time-varying signals $P_1(t)$, $P_2(t)$, $P_3(t)$, ... $P_N(t)$ to the flow logic 36. The flow logic 36 processes the signals $P_1(t)$, $P_2(t)$, $P_3(t)$, ... $P_N(t)$ from the sensors 15 to first provide output signals indicative of the speed of sound propagating through the fluid (process flow) 13, and subsequently, provide output signals in response to pressure disturbances generated by acoustic waves propagating through the process flow 13, such as velocity, Mach number and volumetric flow rate of the process flow 13.

The signal processor 19 receives the pressure signals from the array 11 of sensors 15. A data acquisition unit 138 digitizes the pressure signals $P_1(t) \ldots P_N(t)$ associated with the acoustic waves 122 propagating through the pipe 14. Similarly to the FFT logic 128 of FIG. 20, an FFT logic 140 calculates the Fourier transform of the digitized time-based input signals $P_1(t) \ldots P_N(t)$ and provides complex frequency domain (or frequency based) signals $P_1(\omega)$, $P_2(\omega)$, $P_3(\omega), \ldots P_N(\omega)$ indicative of the frequency content of the input signals.

A data accumulator 142 accumulates the frequency signals $P_1(\omega) \ldots P_N(\omega)$ over a sampling interval, and provides the data to an array processor 144, which performs a spatial-temporal (two-dimensional) transform of the sensor data, from the xt domain to the k-ω domain, and then calculates the power in the k-ω plane, as represented by a k-ω plot.

To calculate the power in the k-ω plane, as represented by a k-ω plot (see FIG. 24) of either the signals or the differenced signals, the array processor 144 determines the wavelength and so the (spatial) wavenumber k, and also the (temporal) frequency and so the angular frequency ω, of various of the spectral components of the stochastic parameter. There are numerous algorithms available in the public domain to perform the spatial/temporal decomposition of arrays of sensor units 15.

Figure 24:
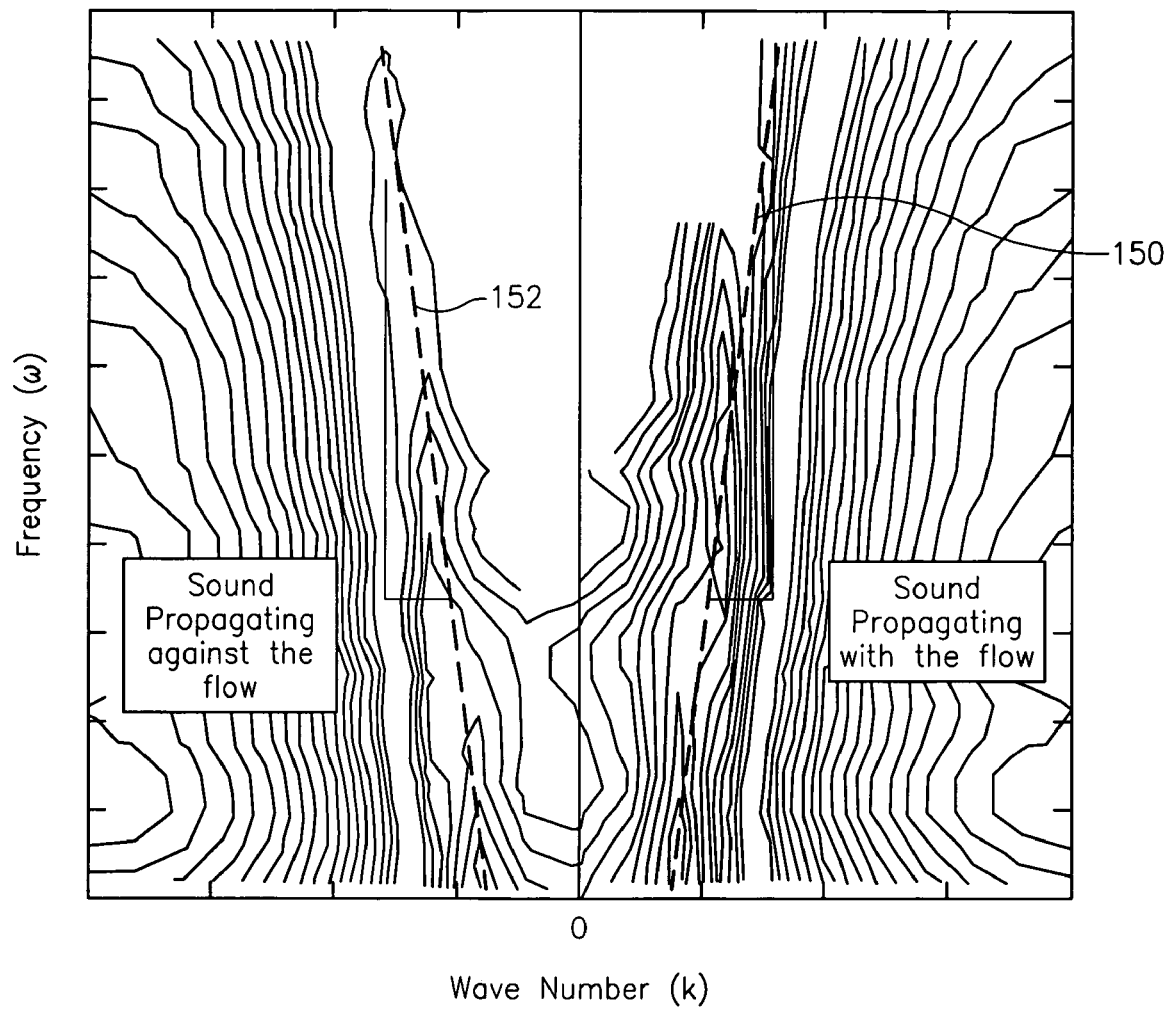
FIG. 24 a kω plot of data processed from an apparatus embodying the present invention that illustrates slope of the acoustic ridges, in accordance with an embodiment of the present invention.

In the case of suitable acoustic waves 122 being present in both axial directions, the power in the k-ω plane shown in a k-ω plot of FIG. 24 so determined will exhibit a structure that is called an acoustic ridge 150, 152 in both the left and right planes of the plot, wherein one of the acoustic ridges 150 is indicative of the speed of sound traveling in one axial direction and the other acoustic ridge 152 being indicative of the speed of sound traveling in the other axial direction. The acoustic ridges represent the concentration of a stochastic parameter that propagates through the flow and is a mathematical manifestation of the relationship between the spatial variations and temporal variations described above. Such a plot will indicate a tendency for k-ω pairs to appear more or less along a line 150, 152 with some slope, the slope indicating the speed of sound.

The power in the k-ω plane so determined is then provided to an acoustic ridge identifier 146, which uses one or another feature extraction method to determine the location and orientation (slope) of any acoustic ridge present in the left and right k-ω plane. The velocity may be determined by using the slope of one of the two acoustic ridges 150, 152 or averaging the slopes of the acoustic ridges 150, 152.

Finally, information including the acoustic ridge orientation (slope) is used by an analyzer 148 to determine the flow parameters relating to measured speed of sound, such as the consistency or composition of the flow, the density of the flow, the average size of particles in the flow, the air/mass ratio of the flow, gas volume fraction of the flow, the speed of sound propagating through the flow, and/or the percentage of entrained air within the flow.

Similar to the array processor 132 of FIG. 20, the array processor 144 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where $\lambda$ is the wavelength of a spectral component, and corresponding angular frequencies given by $\omega=2\pi\nu$.

One such technique of determining the speed of sound propagating through the process flow 13 is using array processing techniques to define an acoustic ridge in the k-ω plane as shown in FIG. 24. The slope of the acoustic ridge is indicative of the speed of sound propagating through the process flow 13. The speed of sound (SOS) is determined by applying sonar arraying processing techniques to determine the speed at which the one dimensional acoustic waves propagate past the axial array of unsteady pressure measurements distributed along the pipe 14.

The flow logic 36 of the present embodiment measures the speed of sound (SOS) of one-dimensional sound waves propagating through the process flow 13 to determine the gas volume fraction of the process flow 13. It is known that sound propagates through various mediums at various speeds in such fields as SONAR and RADAR fields. The speed of sound propagating through the pipe 14 and process flow 13 may be determined using a number of known techniques, such as those set forth in U.S. patent application Ser. No. 09/344,094, filed Jun. 25, 1999, now U.S. Pat. No. 6,354,147; U.S. patent application Ser. No. 10/795,111, filed Mar. 4, 2004; U.S. patent application Ser. No. 09/997,221, filed Nov. 28, 2001, now U.S. Pat. No. 6,587,798; U.S. patent application Ser. No. 10/007,749, filed Nov. 7, 2001, and U.S. patent application Ser. No. 10/762,410, filed Jan. 21, 2004, each of which are incorporated herein by reference.

While the sonar-based flow meter using an array of sensors 15 to measure the speed of sound of an acoustic wave propagating through the mixture is shown and described, one will appreciate that any means for measuring the speed of sound of the acoustic wave may used to determine the entrained gas volume fraction of the mixture/fluid or other characteristics of the flow described hereinbefore.

The analyzer 148 of the flow logic 36 provides output parameters 21 indicative of characteristics of the process flow 13 that are related to the measured speed of sound (SOS) propagating through the process flow 13. For example, to determine the gas volume fraction (or phase fraction), the analyzer 148 assumes a nearly isothermal condition for the process flow 13. As such the gas volume fraction or the void fraction is related to the speed of sound by the following quadratic equation:

$$Ax^2+Bx+C=0$$

wherein x is the speed of sound, $A=1+rg/rl*(K_{eff}/P-1)-K_{eff}/P$, $B=K_{eff}/P-2+rg/rl$; $C=1-K_{eff}/rl*a_{meas}^2)$; Rg=gas density, rl=liquid density, $K_{eff}$=effective K (modulus of the liquid and pipewall), P=pressure, and $a_{meas}$=measured speed of sound.

Effectively, $$\text{Gas Volume Fraction (GVF)}=(-B+sqrt(B^2-4*A*C))/(2*A)$$

Alternatively, the sound speed of a mixture can be related to volumetric phase fraction ($\Phi_i$) of the components and the sound speed (a) and densities (ρ) of the component through the Wood equation.

$$\frac{1}{\rho_{mix} a_{mix_\infty}^2} = \sum_{i=1}^{N} \frac{\phi_i}{\rho_i a_i^2} \quad \text{where} \quad \rho_{mix} = \sum_{i=1}^{N} \rho_i \phi_i$$

One dimensional compression waves propagating within a process flow 13 contained within a pipe 14 exert an unsteady internal pressure loading on the pipe. The degree to which the pipe displaces as a result of the unsteady pressure loading influences the speed of propagation of the compression wave. The relationship among the infinite domain speed of sound and density of a mixture; the elastic modulus (E), thickness (t), and radius (R) of a vacuum-backed cylindrical conduit; and the effective propagation velocity ($a_{eff}$) for one dimensional compression is given by the following expression:

$$a_{eff} = \frac{1}{\sqrt{\frac{1}{a_{mix_\infty}^2} + \rho_{mix}\frac{2R}{Et}}} \quad \text{(eq 1)}$$

Figure 25:
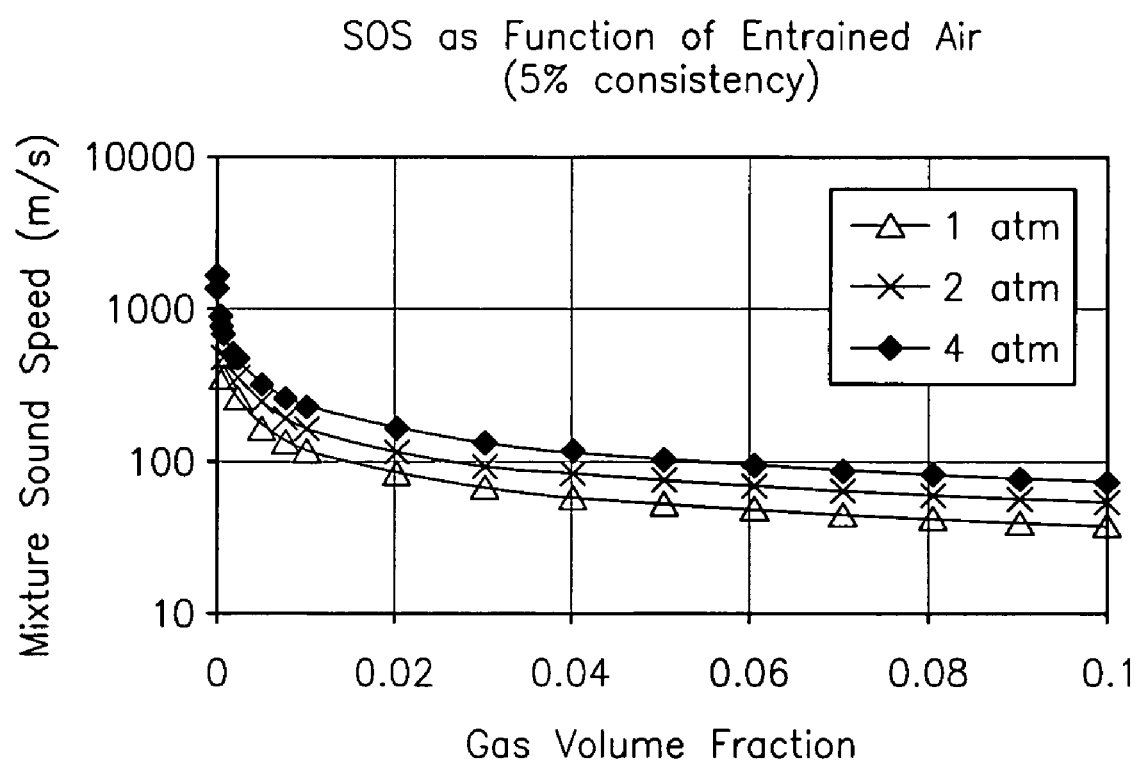
FIG. 25 is a plot of mixture sound speed as a function of gas volume fraction for a 5% consistency slurry over a range of process pressures, in accordance with an embodiment of the present invention.

The mixing rule essentially states that the compressibility of a process flow ($1/(\rho a^2)$) is the volumetrically-weighted average of the compressibilities of the components. For a process flow 13 consisting of a gas/liquid mixture at pressure and temperatures typical of paper and pulp industry, the compressibility of gas phase is orders of magnitudes greater than that of the liquid. Thus, the compressibility of the gas phase and the density of the liquid phase primarily determine mixture sound speed, and as such, it is necessary to have a good estimate of process pressure to interpret mixture sound speed in terms of volumetric fraction of entrained gas. The effect of process pressure on the relationship between sound speed and entrained air volume fraction is shown in FIG. 25.

As described hereinbefore, the flow logic 36 of the present embodiment includes the ability to accurately determine the average particle size of a particle/air or droplet/air mixture within the pipe 14 and the air to particle ratio. Provided there is no appreciable slip between the air and the solid coal particle, the propagation of one dimensional sound wave through multiphase mixtures is influenced by the effective mass and the effective compressibility of the mixture. For an air transport system, the degree to which the no-slip assumption applies is a strong function of particle size and frequency. In the limit of small particles and low frequency, the no-slip assumption is valid. As the size of the particles increases and the frequency of the sound waves increase, the non-slip assumption becomes increasing less valid. For a given average particle size, the increase in slip with frequency causes dispersion, or, in other words, the sound speed of the mixture to change with frequency. With appropriate calibration the dispersive characteristic of a process flow 13 will provide a measurement of the average particle size, as well as, the air to particle ratio (particle/fluid ratio) of the process flow 13.

In accordance with the present invention the dispersive nature of the system utilizes a first principles model of the interaction between the air and particles. This model is viewed as being representative of a class of models that seek to account for dispersive effects. Other models could be used to account for dispersive effects without altering the intent of this disclosure (for example, see the paper titled "Viscous Attenuation of Acoustic Waves in Suspensions" by R. L. Gibson, Jr. and M. N. Toksöz), which is incorporated herein by reference. The model allows for slip between the local velocity of the continuous fluid phase and that of the particles.

The following relation can be derived for the dispersive behavior of an idealized fluid particle mixture.

$$a_{mix}(\omega) = a_f \sqrt{\frac{1}{1 + \frac{\varphi_p \rho_p}{\rho_f \left(1 + \omega^2 \frac{\rho_p^2 v_p^2}{K^2}\right)}}}$$

In the above relation, the fluid SOS, density (ρ) and viscosity (Φ) are those of the pure phase fluid, $v_p$ is the volume of individual particles and $\square_p$ is the volumetric phase fraction of the particles in the mixture.

Figure 26:
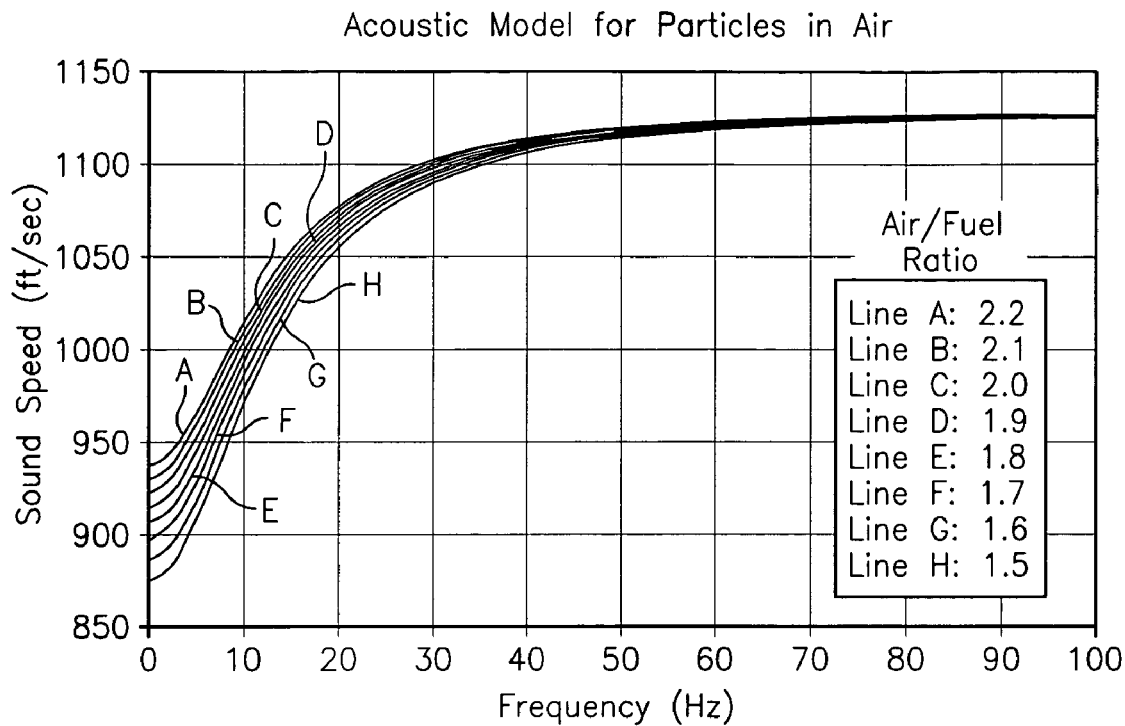
FIG. 26 is a plot of sound speed as a function of frequency for air/particle mixtures with fixed particle size and varying air-to-particle mass ratio, in accordance with an embodiment of the present invention.
Figure 27:
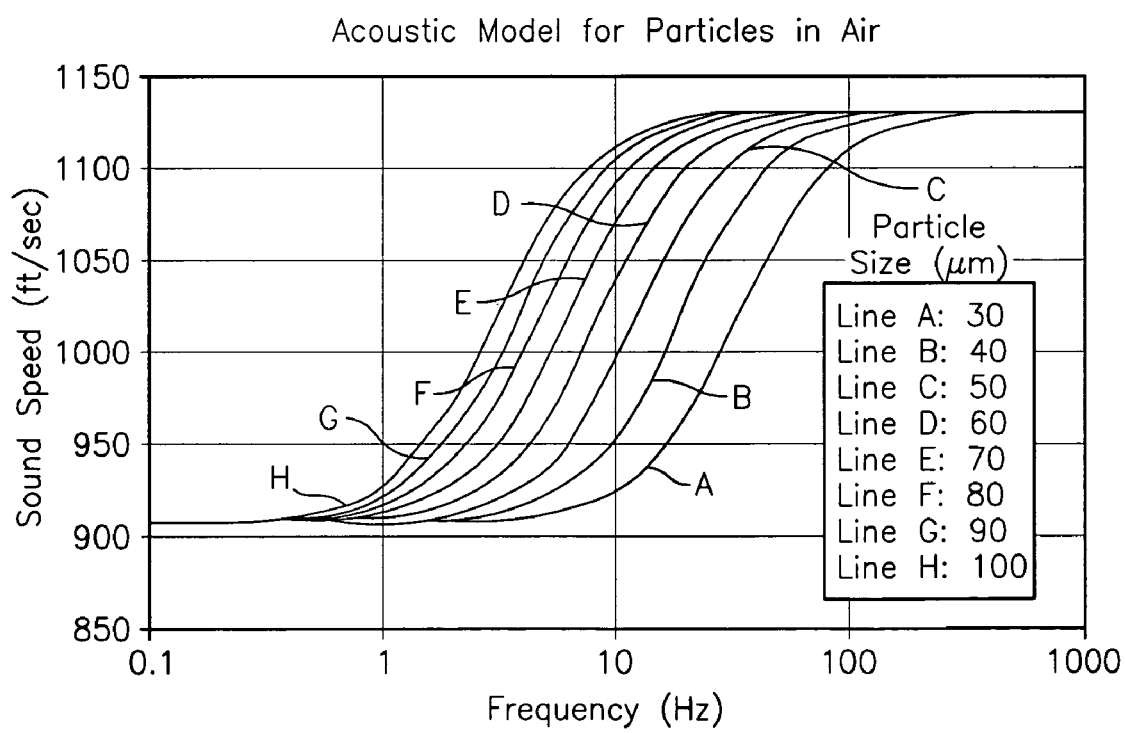
FIG. 27 is a plot of sound speed as a function of frequency for air/particle mixtures with varying particle size where the air-to-particle mass ratio is fixed, in accordance with an embodiment of the present invention.

Two parameters of particular interest in steam processes and air-conveyed particles processes are particle size and air-to-fuel mass ratio or steam quality. To this end, it is of interest to examine the dispersive characteristics of the mixture as a function of these two variables. FIG. 26 and FIG. 27 show the dispersive behavior in relations to the speed of sound for coal/air mixtures with parameters typical of those used in pulverized coal deliver systems.

In particular FIG. 26 shows the predicted behavior for nominally 50 micrometer size coal in air for a range of air-to-fuel ratios. As shown, the effect of air-to-fuel ratio is well defined in the low frequency limit. However, the effect of the air-to-fuel ratio becomes indistinguishable at higher frequencies, approaching the sound speed of the pure air at high frequencies (above ~100 Hz).

Similarly, FIG. 27 shows the predicted behavior for a coal/air mixture with an air-to-fuel ratio of 1.8 with varying particle size. This figure illustrates that particle size has no influence on either the low frequency limit (quasi-steady) sound speed, or on the high frequency limit of the sound speed. However, particle size does have a pronounced effect in the transition region.

FIG. 26 and FIG. 27 illustrate an important aspect of the present invention. Namely, that the dispersive properties of dilute mixtures of particles suspended in a continuous liquid can be broadly classified into three frequency regimes: low frequency range, high frequency range and a transitional frequency range. Although the effect of particle size and air-to-fuel ratio are inter-related, the predominant effect of air-to-fuel ratio is to determine the low frequency limit of the sound speed to be measured and the predominate effect of particle size is to determine the frequency range of the transitional regions. As particle size increases, the frequency at which the dispersive properties appear decreases. For typical pulverized coal applications, this transitional region begins at fairly low frequencies, ~2 Hz for 50 micrometer size particles.

Given the difficulties measuring sufficiently low frequencies to apply the quasi-steady model and recognizing that the high frequency sound speed contains no direct information on either particle size or air-to-fuel ratio, it becomes apparent that the dispersive characteristics of the coal/air mixture should be utilized to determine particle size and air-to-fuel ratio based on speed of sound measurements.

Some or all of the functions within the flow logic 36 may be implemented in software (using a microprocessor or computer) and/or firmware, or may be implemented using analog and/or digital hardware, having sufficient memory, interfaces, and capacity to perform the functions described herein.

While FIG. 20 and FIG. 23 depict two different embodiments of the flow logic 36 to measure various parameters of the flow process, the present invention contemplates that the functions of these two embodiments may be performed by a single flow logic 36.

EXAMPLES

Figure 28:
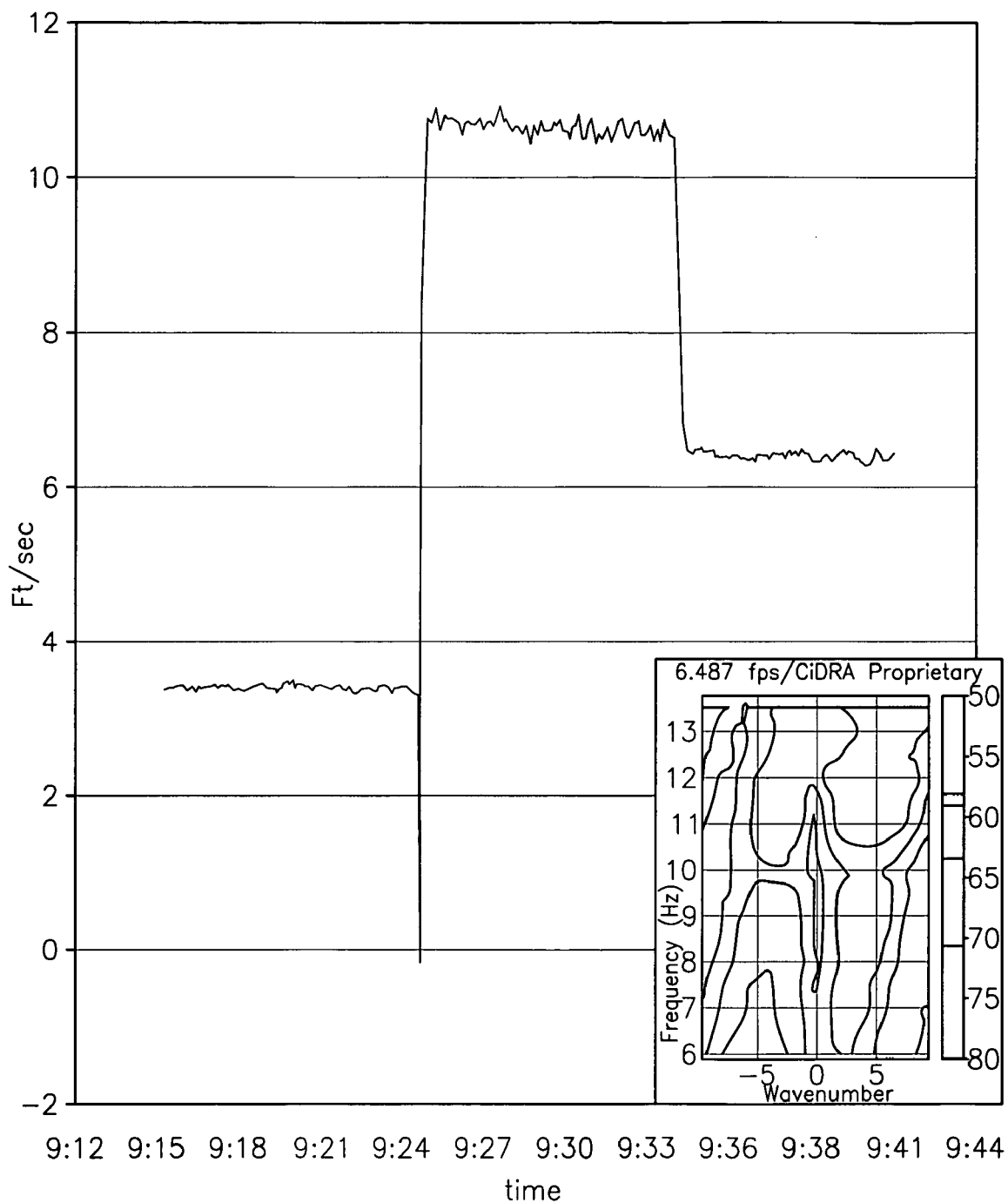
FIG. 28 is a plot of flow rate (ft/sec) as a function of time as output from an apparatus in accordance with an embodiment of the present invention, and a corresponding kω plot from the apparatus, in accordance with an embodiment of the present invention.

FIG. 28 shows outputs from an apparatus of the present invention including five helically wrapped, 4" spaced, 10 foot long PVDF cables of circular cross-section (as shown in FIG. 1) on 8" Schedule 40 pipe. In FIG. 28, flow rate in ft/sec is shown for about 3.5 ft/sec, about 11 ft/sec, and about 6.5 ft/sec over various test periods. The lower right corner of FIG. 28 shows a representative $k\omega$ plot output from the apparatus. As can be seen in FIG. 28, the flow measurements all have a standard deviation of 1% of average, which confirms the accuracy and legitimacy of the data from the array of sensors used in the apparatus of the present invention.

It should be understood that, unless stated otherwise herein, any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein without departing from the spirit and scope of the present invention.

What is claimed is:

1. An apparatus comprising:
   a cable disposed on a portion of a pipe, wherein the cable provides a signal indicative of unsteady pressures within the pipe, the cable including:
      a first electrical conductor,
      a piezoelectric material disposed around the first electrical conductor, and
      a second electrical conductor disposed around the piezoelectric material.

2. The apparatus of claim 1, further comprising a band disposed on the cable, wherein the band compresses the cable toward the pipe and the cable provides a signal indicative of unsteady pressure within the pipe.

3. The apparatus of claim 1, wherein the cable is wrapped around the pipe at least one time.

4. The apparatus of claim 1, further comprising:
   a signal processor configured to determine a parameter of the fluid using the signal from the cable.

5. The apparatus of claim 4, wherein the parameter of the fluid includes at least one of: density of the fluid, volumetric flow rate of the fluid, mass flow rate of the fluid, composition of the fluid, entrained air in the fluid, consistency of the fluid, size of particles in the fluid, and health of a device causing the unsteady pressures to be generated in the pipe.

6. The apparatus of claim 1, wherein the cable has one of a circular cross section, a quadrilateral cross section, a polygonal cross section and a rounded cross section.

7. The apparatus of claim 1, further comprising:
   an alignment sheet disposed between the cable and the pipe, the alignment sheet including tabs protruding therefrom in a direction away from the pipe, the tabs defining a raceway for receiving the cable.

8. The apparatus of claim 7, wherein the alignment sheet further includes:
   a cable inlet bumper attached to the alignment sheet, the cable inlet bumper being positioned on a first side of the sensor raceway and having a radiused surface formed thereon around which a first end of the cable is bent; and
   a cable exit bumper attached to the alignment sheet, the cable exit bumper being positioned on a second side of the sensor raceway opposite the first side of the sensor raceway and having a radiused surface formed thereon around which a second end of the cable is bent.

9. The apparatus of claim 7, further comprising:
   an electrical insulator disposed between the alignment sheet and the pipe.

10. The apparatus of claim 1, wherein the cable is one of an array of cables disposed on the pipe, each cable in the array of cables providing a pressure signal indicative of unsteady pressure within the pipe at a corresponding axial location spaced along the pipe.

11. The apparatus of claim 10, further comprising:
    a signal processor configured to determine a parameter of the fluid using the signals from the array of cables.

12. The apparatus of claim 11, wherein the parameter of the fluid includes at least one of: density of the fluid, volumetric flow rate of the fluid, mass flow rate of the fluid, composition of the fluid, entrained air in the fluid, consistency of the fluid, size of particles in the fluid, and health of a device causing the unsteady pressures to be generated in the pipe.

13. The apparatus of claim 1, wherein the piezoelectric material includes polyvinylidene fluoride (PVDF).

14. A method of installing an apparatus for measuring at least one parameter of a fluid flowing within a pipe, the method comprising:
    (a) wrapping cable wrapped around at least a portion of a pipe, the cable including:
       a first electrical conductor,
       a piezoelectric material disposed around the first electrical conductor,
       a second electrical conductor disposed around the piezoelectric material, and
    (b) electrically connecting the cable to a signal processor, wherein the cable provides a signal indicative of unsteady pressure within the pipe, and the signal processor determines a parameter of the fluid using the signal from the cable.

15. The method of claim 14, further comprising:
    (c) wrapping a band around the cable; and
    (d) tightening the band around the cable to compress the cable toward the pipe.

16. The method of claim 14, wherein the parameter of the fluid includes at least one of density of the fluid, volumetric flow rate of the fluid, mass flow rate of the fluid, composition of the fluid, entrained air in the fluid, consistency of the fluid, size of particles in the fluid, and health of a device causing the unsteady pressures to be generated in the pipe.

17. The method of claim 14, wherein the cable has one of: a circular cross section, a quadrilateral cross section, a polygonal cross section and a rounded cross section.

18. The method of claim 14, further comprising:
    before wrapping the cable, attaching an alignment sheet to the pipe, the alignment sheet including tabs protruding therefrom in a direction away from the pipe, the tabs defining a raceway for receiving the cable.

19. The method of claim 14, further comprising:
    repeating (a) through (b) for each cable in a plurality of cables to form an array of cables wrapped around the pipe, wherein each cable in the array of cables provides a pressure signal indicative of unsteady pressure within the pipe at a corresponding axial location along the pipe, and the signal processor determines the parameter of the fluid using the signals from the array of cables.

20. The method of claim 19, wherein the parameter of the fluid includes at least one of: density of the fluid, volumetric flow rate of the fluid, mass flow rate of the fluid, composition of the fluid, entrained air in the fluid, consistency of the fluid, size of particles in the fluid, and health of a device causing the unsteady pressures to be generated in the pipe.

21. The method of claim 14, wherein wrapping a cable wrapped around the pipe includes wrapping the cable around the pipe at least one times.

22. The method of claim 14, wherein the piezoelectric material includes polyvinylidene fluoride (PVDF).

23. The apparatus of claim 1, wherein the cable is wrapped circumferentially around at least a portion of the pipe.

24. The apparatus of claim 23, wherein the cable is wrapped circumferentially around the pipe at least once.

25. The apparatus of claim 24, wherein the cable is wrapped circumferentially around the pipe a plurality of times.

26. The apparatus of claim 25, wherein a band is wrapped around the cable to compress the cable towards the pipe.

27. The apparatus of claim 26, wherein the band is clamped over the cable to compress the cable towards the pipe.

28. The apparatus of claim 1, wherein the cable is compressed against the pipe by a support.

29. The apparatus of claim 28, wherein the support is a band.

30. The method of claim 18, further comprising:
wrapping an electrical insulator around the pipe, the electrical insulator being disposed between the alignment sheet and the pipe.

31. An apparatus for measuring a parameter of a fluid flowing in a pipe; the apparatus comprising:
a plurality of cables disposed on a portion of the pipe, the cables being axially spaced along the pipe, wherein each of the cables provides a signal indicative of unsteady pressures within the pipe at each respective axial location, each cable including:
a first electrical conductor,
a piezoelectric material disposed around the first electrical conductor, and
a second electrical conductor disposed around the piezoelectric material.

32. The apparatus of claim 31, further comprising a band or bands disposed on each respective cable, wherein the band compresses the respective cable toward the pipe and each respective cable provides a signal indicative of unsteady pressure within the pipe at the respective location of the pipe.

33. The apparatus of claim 31, wherein each cable is wrapped around the pipe at least one time.

34. The apparatus of claim 31, further comprising:
a signal processor configured to determine a parameter of the fluid using the signals from the cables.

35. The apparatus of claim 34, wherein the parameter of the fluid includes at least one of: density of the fluid, volumetric flow rate of the fluid, mass flow rate of the fluid, composition of the fluid, entrained air in the fluid, consistency of the fluid, size of particles in the fluid, and health of a device causing the unsteady pressures to be generated in the pipe.

36. The apparatus of claim 31, wherein the cables have one of a circular cross section, a quadrilateral cross section, a polygonal cross section and a rounded cross section.

37. The apparatus of claim 31, further comprising:
an alignment sheet disposed between the cables and the pipe, the alignment sheet including tabs protruding therefrom in a direction away from the pipe, the tabs defining a raceway for receiving each respective cable.

38. The apparatus of claim 37, wherein the alignment sheet further includes:
cable inlet bumpers attached to the alignment sheet, the cable inlet bumpers being positioned on a first side of the sensor raceway and having a radiused surface formed thereon around which a first end of a respective cable is bent; and
cable exit bumpers attached to the alignment sheet, the cable exit bumpers being positioned on a second side of the sensor raceway opposite the first side of the respective sensor raceway and having a radiused surface formed thereon around which a second end of the respective cable is bent.

39. The apparatus of claim 37, further comprising:
an electrical insulator disposed between the alignment sheet and the pipe.

40. The apparatus of claim 31, wherein the piezoelectric material includes polyvinylidene fluoride (PVDF).

41. The apparatus of claim 31, wherein each cable is wrapped circumferentially around at least a portion of the pipe.

42. The apparatus of claim 41, wherein each cable is wrapped circumferentially around the pipe at least once.

43. The apparatus of claim 42, wherein each cable is wrapped circumferentially around the pipe a plurality of times.

44. The apparatus of claim 31, wherein each cable is compressed against the pipe by a support.

45. The apparatus of claim 44, wherein the support is a band.

46. The apparatus of claim 34, the signal processor defines a convective ridge in the k-$\omega$ plane in response to the signals, and determines the slope of at least a portion of the convective ridge to determine the flow velocity of the fluid.

47. The apparatus of claim 31, wherein the signals are indicative of vertical disturbances within the fluid.

48. The apparatus of claim 46, wherein the processor uses a beam forming algorithm to define the convective ridge in the k-$\omega$ plane.

49. The apparatus of claim 48, wherein the beam forming algorithm includes one of a Capon algorithm and a MUSIC algorithm.

50. The apparatus of claim 31, wherein the plurality of cables comprise at least 4, 5, 6, 7, 8, 9, 10, 11, 12, 13, 14, 15,or 16 cables.

51. The apparatus of claim 34, wherein the processor uses an array processing algorithm.

52. The apparatus of claim 31, wherein the plurality of cables comprise two cables.

53. The apparatus of claim 31, wherein the plurality of cables comprise three cables.

54. The apparatus of claim 34, the signal processor defines an acoustic ridge in the k-$\omega$ plane in response to the signals, and determines the slope of at least a portion of the acoustic ridge to determine the speed of sound propagating through the fluid.

55. The apparatus of claim 31, wherein the signals are indicative of acoustic signals propagating through the fluid.

56. The apparatus of claim 55, wherein the acoustic signals are planar and propagating axially though the fluid flowing in the pipe.

* * * * *